(12) United States Patent
Ohki et al.

(10) Patent No.: US 7,179,801 B2
(45) Date of Patent: Feb. 20, 2007

(54) CEPHEM COMPOUNDS

(75) Inventors: Hidenori Ohki, Osaka (JP); Shinya Okuda, Osaka (JP); Toshio Yamanaka, Osaka (JP); Takashi Ogino, deceased, late of Osaka (JP); by Hitomi Ogino, legal representative, Toyonaka (JP); by Tetsuya Ogino, legal representative, Kobe (JP); by Tomomi Takezawa, legal representative, Akashi (JP); Kohji Kawabata, Osaka (JP); Satoshi Inoue, Akitakata (JP); Keiji Misumi, Akitakata (JP); Kenji Itoh, Akitakata (JP); Hisashi Akamatsu, Akitakata (JP); Kenji Satoh, Akitakata (JP)

(73) Assignees: Astellas Pharma Inc., Tokyo (JP); Wakunaga Pharmaceutical Co., Ltd., Osaka (JP)

( * ) Notice: Subject to any disclaimer, the term of this patent is extended or adjusted under 35 U.S.C. 154(b) by 160 days.

(21) Appl. No.: 10/475,845

(22) PCT Filed: Apr. 24, 2002

(86) PCT No.: PCT/JP02/04058

§ 371 (c)(1),
(2), (4) Date: Jun. 17, 2004

(87) PCT Pub. No.: WO02/090364

PCT Pub. Date: Nov. 14, 2002

(65) Prior Publication Data

US 2004/0248875 A1    Dec. 9, 2004

(30) Foreign Application Priority Data

May 1, 2001 (JP) .................................. PR 4690
Jun. 20, 2001 (JP) .................................. PR 5834

(51) Int. Cl.
| | | |
|---|---|---|
| C07D 501/46 | (2006.01) | |
| C07D 519/06 | (2006.01) | |
| C07D 501/26 | (2006.01) | |
| A61K 31/546 | (2006.01) | |
| A61P 31/04 | (2006.01) | |

(52) U.S. Cl. ...................... 514/202; 540/222
(58) Field of Classification Search ............ None
See application file for complete search history.

(56) References Cited

U.S. PATENT DOCUMENTS

| | | | | |
|---|---|---|---|---|
| 4,927,818 A | * | 5/1990 | Takaya et al. | 514/202 |
| 4,952,578 A | * | 8/1990 | Sakane et al. | 514/202 |
| 5,109,130 A | * | 4/1992 | Sakane et al. | 540/222 |
| 5,173,485 A | * | 12/1992 | Sakane et al. | 514/202 |
| 5,187,160 A | * | 2/1993 | Sakane et al. | 514/202 |
| 5,194,432 A | | 3/1993 | Takaya et al. | |
| 5,210,080 A | * | 5/1993 | Takaya et al. | 514/202 |
| 5,215,982 A | * | 6/1993 | Sakane et al. | 514/202 |
| 5,302,712 A | * | 4/1994 | Sakane et al. | 540/222 |
| 5,663,163 A | * | 9/1997 | Takaya et al. | 514/202 |
| 2004/0132994 A1 | * | 7/2004 | Ohki et al. | 540/222 |
| 2005/0004094 A1 | * | 1/2005 | Yamanaka et al. | 514/202 |
| 2005/0096306 A1 | * | 5/2005 | Yamanaka et al. | 514/202 |

FOREIGN PATENT DOCUMENTS

| | | |
|---|---|---|
| EP | 0 771 803 | 5/1997 |
| WO | 97 41128 | 11/1997 |

OTHER PUBLICATIONS

Brown, R.F. et al.: "Synthesis and Biological of a Series of Parenteral 3'-Quatemary Ammonium Cephalosporins" Journal of Medicinal Chemistry, vol. 33, 1990, pp. 2114-2121, XP001084083 table I.

Skagami, K. et al.: "Synthetic Cephalosporins. VI. Synthesis and Antibacterial Activity of 7-'(Z)-2-(2-Aminothiazol-4-yl)-2-(1-carboxy-1-methyl)ethoxyiminoacetamidol-3-(3-hydroxy-4-pyridon-1-yl)methyl-3-cephem-4-carboxylic Acid and Related Compounds" Chem. Pharm. Bull., vol. 38, No. 8, 1990, pp. 2271-2273, XP001083825 Chart 2: "Ceftazidime".

* cited by examiner

Primary Examiner—Mark L. Berch
(74) Attorney, Agent, or Firm—Oblon, Spivak, McClelland, Maier & Neustadt, P.C.

(57) ABSTRACT

The present invention relates to a compound of the formula [I]: wherein A is lower alkylene or lower alkenylene; $R^1$ is lower alkyl, hydroxy(lower)alkyl, protected hydroxy(lower)alkyl, amino(lower)alkyl or protected amino(lower)alkyl, and $R^2$ is hydrogen or amino protecting group, or $R^1$ and $R^2$ are bonded together and form lower alkylene; $R^3$ and $R^5$ are independently amino or protected amino; and $R^4$ is carboxy or protected carboxy, or a pharmaceutically acceptable salt thereof, a process for preparing a compound of the formula [I], and a pharmaceutical composition comprising a compound of the formula [I] in admixture with a pharmaceutically acceptable carrier.

11 Claims, No Drawings

CEPHEM COMPOUNDS

TECHNICAL FIELD

The present invention relates to new cephem compounds and pharmaceutically acceptable salts thereof. More particularly, the present invention relates to new cephem compounds and pharmaceutically acceptable salts thereof, which have antimicrobial activities, to processes for preparation thereof, to pharmaceutical composition comprising the same, and to a method for treating infectious diseases in human being and animals.

DISCLOSURE OF INVENTION

One object of the present invention is to provide novel cephem compounds and pharmaceutically acceptable salts thereof, which are highly active against a number of pathogenic microorganisms.

Another object of the present invention is to provide processes for the preparation of said cephem compounds and salts thereof.

A further object of the present invention is to provide a pharmaceutical composition comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

The object cephem compounds of the present invention are novel and can be represented by the following general formula [I]:

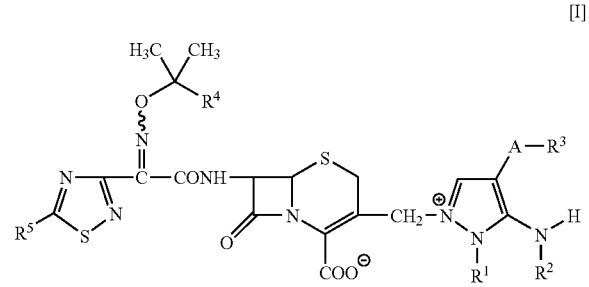

wherein
A is lower alkylene or lower alkenylene;
$R^1$ is lower alkyl, hydroxy(lower)alkyl, protected hydroxy (lower)alkyl, amino(lower)alkyl or protected amino(lower)alkyl, and
$R^2$ is hydrogen or amino protecting group, or
$R^1$ and $R^2$ are bonded together and form lower alkylene;
$R^3$ and $R^5$ are independently amino or protected amino; and
$R^4$ is carboxy or protected carboxy.

As to the object compound [I], the following points are to be noted.

That is, the object compound [I] includes syn isomer (Z form), anti isomer (E form) and a mixture thereof. Syn isomer (Z form) means one geometrical isomer having the partial structure represented by the following formula:

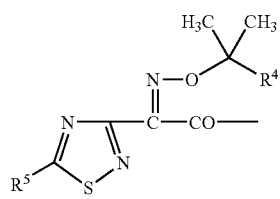

wherein $R^4$ and $R^5$ are each as defined above,
and anti isomer (E form) means the other geometrical isomer having the partial structure represented by the following formula:

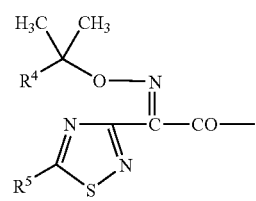

wherein $R^4$ and $R^5$ are each as defined above,
and all of such geometrical isomers and mixture thereof are included within the scope of this invention.

In the present specification and claims, the partial structure of these geometrical isomers and mixture thereof are represented for convenience' sake by the following formula:

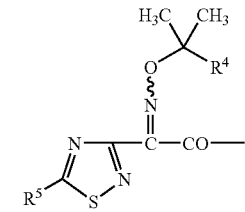

wherein $R^4$ and $R^5$ are each as defined above.

Another point to be noted is that the pyrazolio moiety of the compound [I] can also exist in the tautomeric form, and such tautomeric equilibrium can be represented by the following formula.

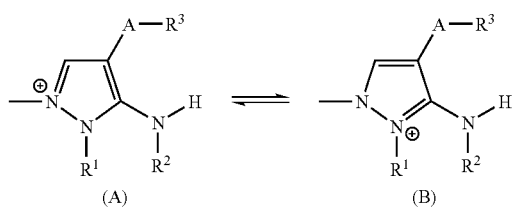

wherein A, $R^1$, $R^2$ and $R^3$ are each as defined above.

Both of the above tautomeric isomers are included within the scope of the present invention, and in the present specification and claims, however, the object compound [I] is represented for convenience' sake by one expression of the pyrazolio group of the formula (A).

The cephem compound [I] of the present invention can be prepared by the following processes as illustrated in the following.
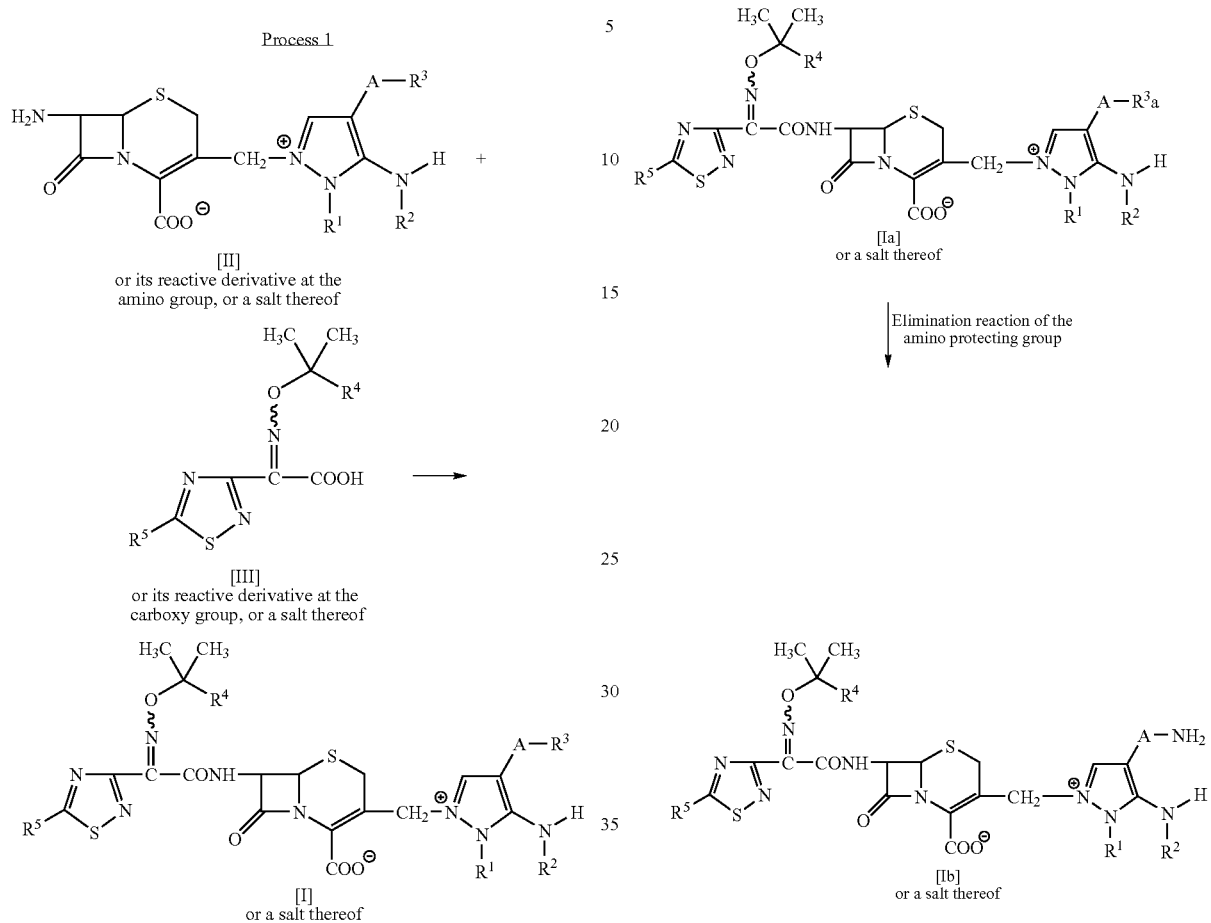
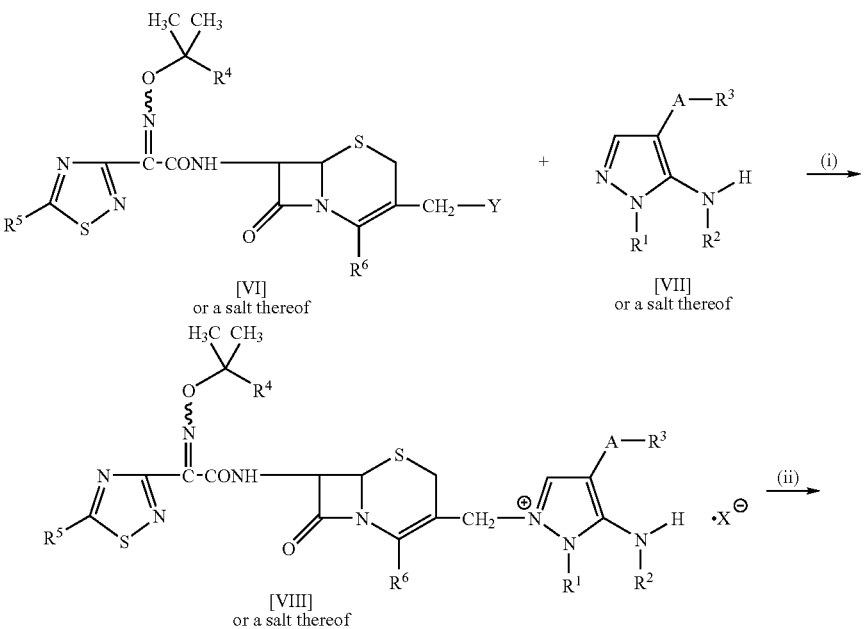

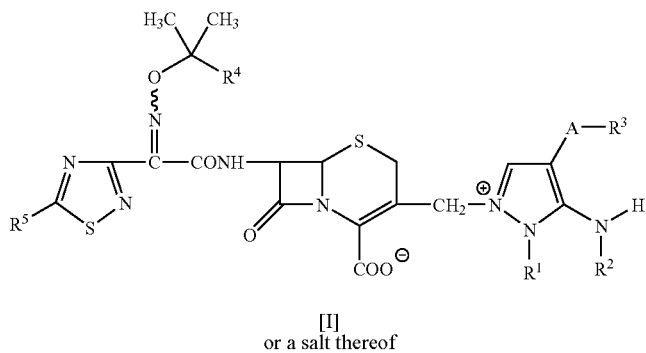

[I]
or a salt thereof

The starting compounds [II] and [VI] can be prepared by the following processes.

Process 4

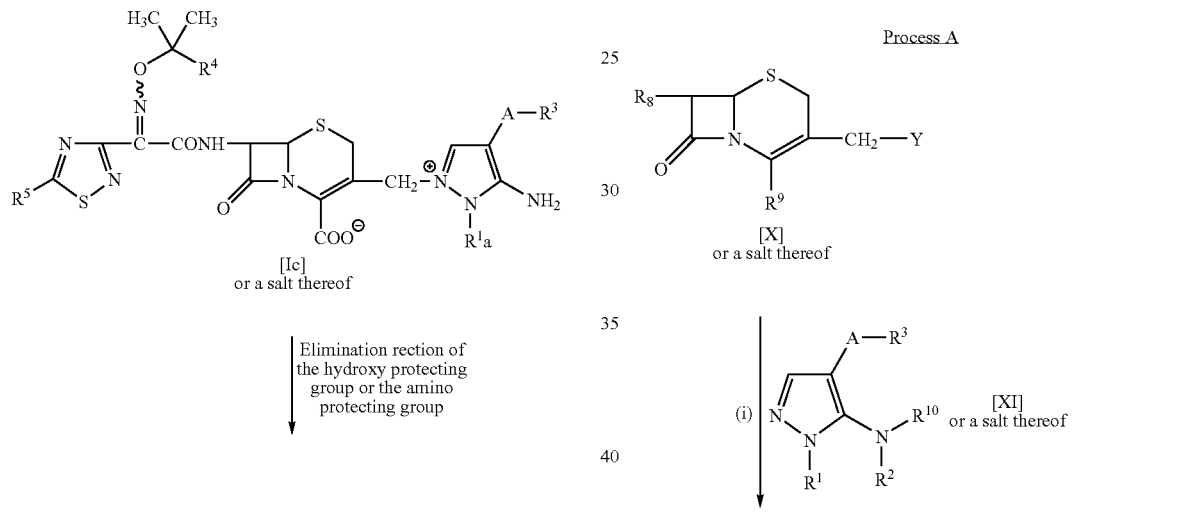

wherein A, $R^1$, $R^2$, $R^3$, $R^4$, and $R^5$ are each as defined above,
$R^3a$ is protected amino,
$R^6$ is protected carboxy,
Y is leaving group,
$X^\ominus$ is an anion,
$R^1a$ is protected hydroxy (lower) alkyl or protected amino (lower) alkyl, and
$R^1b$ is hydroxy (lower) alkyl or amino (lower) alkyl.

Process A

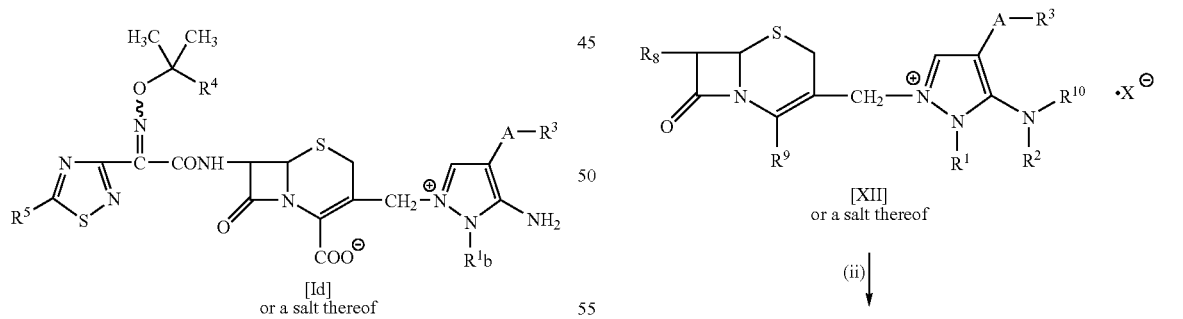

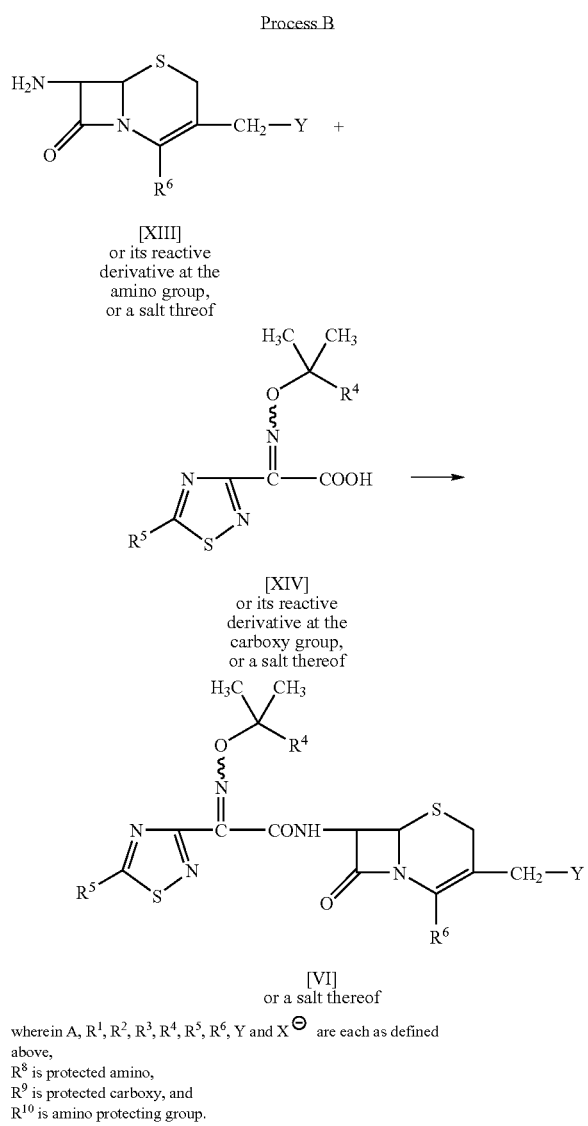

[XIII]
or its reactive derivative at the amino group, or a salt threof

[XIV]
or its reactive derivative at the carboxy group, or a salt thereof

[VI]
or a salt thereof wherein A, $R^1$, $R^2$, $R^3$, $R^4$, $R^5$, $R^6$, Y and $X^\ominus$ are each as defined above,
$R^8$ is protected amino,
$R^9$ is protected carboxy, and
$R^{10}$ is amino protecting group.

The starting compounds [VII] and [XI] or salts thereof can be prepared by the methods disclosed in the Preparations 1–7, 9–14, 16–18, 21–23, 25–45, 47–52, 54, 55, 57–61, 62–66 and 68–76 described later or similar manners thereto.

In the above and subsequent descriptions of this specification, suitable examples of the various definitions are explained in detail as follows.

The term "lower" is used to mean a group having 1 to 6, preferably 1 to 4, carbon atom(s), unless otherwise indicated.

Suitable "lower alkyl" and "lower alkyl" moiety in "hydroxy(lower)alkyl", "protected hydroxy(lower)alkyl", "amino(lower)alkyl" and "protected amino(lower)alkyl" include straight or branched alkyl having 1 to 6 carbon atom(s), such as methyl, ethyl, propyl, isopropyl, butyl, isobutyl, sec-butyl, tert-butyl, pentyl, tert-pentyl and hexyl, in which more preferred one is $C_1$–$C_4$ alkyl.

Suitable "hydroxy(lower)alkyl" includes hydroxy($C_1$–$C_6$) alkyl such as hydroxymethyl, 1-hydroxyethyl, 2-hydroxyethyl, 1-hydroxypropyl, 2-hydroxypropyl, 3-hydroxypropyl, 4-hydroxybutyl, 5-hydroxypentyl and 6-hydroxyhexyl, in which more preferred one is hydroxy($C_1$–$C_4$)alkyl.

Suitable "amino(lower)alkyl" includes amino($C_1$–$C_6$) alkyl such as aminomethyl, 1-aminoethyl, 2-aminoethyl, 1-aminopropyl, 2-aminopropyl, 3-aminopropyl, 4-aminobutyl, 5-aminopentyl and 6-aminohexyl, in which more preferred one is amino($C_1$–$C_4$)alkyl.

Suitable "lower alkylene" at A includes straight or branched alkylene having 1 to 6 carbon atoms, such as methylene, ethylene, trimethylene, tetramethylene, pentamethylene, hexamethylene and propylene, in which more preferred one is straight alkylene having 1 to 3 carbon atoms.

Suitable "lower alkenylene" at A includes straight or branched alkenylene having 2 to 6 carbon atoms, such as vinylene, propenylene, 1-butenylene, 2-butenylene, 1-pentenylene, 2-pentenylene, 1-hexenylene, 2-hexenylene, 3-hexenylene, in which more preferred one is straight alkenylene having 2 or 3 carbon atoms.

Suitable "lower alkylene" formed by $R^1$ and $R^2$ includes straight alkylene having 2 to 4 carbon atoms, such as ethylene, trimethylene and tetramethylene, in which more preferred one is straight alkylene having 2 or 3 carbon atoms.

Suitable "amino protecting group" in "protected amino" and "protected amino(lower)alkyl" includes an acyl group as mentioned below, substituted or unsubstituted aryl(lower) alkylidene [e.g., benzylidene, hydroxybenzylidene, etc.], aryl(lower)alkyl such as mono-, di- or triphenyl(lower)alkyl [e.g., benzyl, phenethyl, benzhydryl, trityl, etc.], and the like.

Suitable "acyl" includes lower alkanoyl [e.g., formyl, acetyl, propionyl, hexanoyl, pivaloyl, etc.], mono(or di or tri)halo(lower)alkanoyl [e.g., chloroacetyl, trifluoroacetyl, etc.], lower alkoxycarbonyl [e.g., methoxycarbonyl, ethoxycarbonyl, tert-butoxycarbonyl, tert-pentyloxycarbonyl, hexyloxycarbonyl, etc.], carbamoyl, aroyl [e.g., benzoyl, toluoyl, naphthoyl, etc.], aryl(lower)alkanoyl [e.g., phenylacetyl, phenylpropionyl, etc.], aryloxycarbonyl [e.g., phenoxycarbonyl, naphthyloxycarbonyl, etc.], aryloxy(lower) alkanoyl [e.g., phenoxyacetyl, phenoxypropionyl, etc.], arylglyoxyloyl [e.g., phenylglyoxyloyl, naphthylglyoxyloyl, etc.], aryl(lower)alkoxycarbonyl which optionally substituted by suitable substituent(s) [e.g., benzyloxycarbonyl, phenethyloxycarbonyl, p-nitrobenzyloxycarbonyl, etc.], and the like.

Suitable "protected hydroxy" in the "protected hydroxy (lower)alkyl" includes acyloxy group, aryl(lower)alkyloxy group, and the like. Suitable "acyl" moiety in the "acyloxy" includes lower alkanoyl [e.g., formyl, acetyl, propionyl, hexanoyl, pivaloyl, etc.], mono(or di or tri)halo(lower)alkanoyl, [e.g., chloroacetyl, trifluoroacetyl, etc.], lower alkoxycarbonyl, [e.g., methoxycarbonyl, ethoxycarbonyl, tert-butoxycarbonyl, tert-pentyloxycarbonyl, hexyloxycarbonyl, etc.], carbamoyl, and the like. Suitable "aryl(lower) alkyl" moiety in the "aryl(lower)alkyloxy" includes mono-, di- or triphenyl(lower)alkyl [e.g., benzyl, phenethyl, benzhydryl, trityl, etc.], and the like.

Suitable "protected carboxy" includes an esterified carboxy group and the like, and concrete examples of the ester moiety in said esterified carboxy group include the ones such as lower alkyl ester [e.g., methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g., acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, 2-propionyloxyethyl ester, hexanoyloxymethyl ester, etc.], lower alkanesulfonyl(lower)alkyl ester, [e.g., 2-mesylethyl ester, etc.] or mono(or di or tri)halo(lower)alkyl ester [e.g., 2-iodoethyl ester, 2,2,2-trichloroethyl ester, etc.]; lower alkenyl ester [e.g., vinyl ester, allyl ester, etc.]; lower alkynyl ester [e.g., ethynyl ester, propynyl ester, etc.]; aryl(lower)alkyl ester which may have suitable substituent(s) [e.g., benzyl ester, 4-methoxybenzyl ester, 4-nitrobezyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.]; aryl ester which may have suitable substituent(s) [e.g., phenyl ester, 4-chlorophenyl ester, tolyl ester, 4-tert-butylphenyl ester, xylyl ester, mesityl ester, cumenyl ester, etc.]; and the like.

Suitable "leaving group" includes halogen [e.g., chlorine, bromine, iodine, etc.] or acyloxy such as arylsulfonyloxy [e.g., benzenesulfonyloxy, tosyloxy, etc.], lower alkylsulfonyloxy [e.g., mesyloxy, etc.], lower alkanoyloxy [e.g., acetyloxy, propionyloxy, etc.], and the like.

Suitable "anion" includes formate, acetate, trifluoroacetate, maleate, tartrate, methanesulfonate, benzenesulfonate, toluenesulfonate, chloride, bromide, iodide, sulfate, hydrogensulfate, phosphate, and the like.

Suitable pharmaceutically acceptable salts of the object compound [I] are conventional non-toxic salts and include, for example, a salt with a base or an acid addition salt such as a salt with an inorganic base, for example, an alkali metal salt [e.g., sodium salt, potassium salt, etc.], an alkaline earth metal salt [e.g., calcium salt, magnesium salt, etc.], an ammonium salt; a salt with an organic base, for example, an organic amine salt [e.g., trimethylamine salt, triethylamine salt, pyridine salt, picoline salt, ethanolamine salt, triethanolamine salt, dicyclohexylamine salt, N,N'-dibenzylethylenediamine salt, etc.]; an inorganic acid addition salt [e.g., hydrochloride, hydrobromide, sulfate, hydrogensulfate, phosphate, etc.]; an organic carboxylic or sulfonic acid addition salt [e.g., formate, acetate, trifluoroacetate, maleate, tartrate, citrate, fumarate, methanesulfonate, benzenesulfonate, toluenesulfonate, etc.]; and a salt with a basic or acidic amino acid [e.g., arginine, aspartic acid, glutamic acid, etc.].

The preferred embodiments of the cephem compound of the present invention represented by the general formula [I] are as follows.

(1) The compound of the formula [I] wherein
$R^1$ is lower alkyl, hydroxy(lower)alkyl, aryl(lower)alkyloxy (lower)alkyl, amino(lower)alkyl or acylamino(lower)alkyl, and
$R^2$ is hydrogen, aryl(lower)alkyl or acyl, or
$R^1$ and $R^2$ are bonded together and form lower alkylene;
$R^3$ and $R^5$ are independently amino or acylamino; and
$R^4$ is carboxy or esterified carboxy,
or a pharmaceutically acceptable salt thereof.

(2) The compound of (1) above wherein
$R^1$ is lower alkyl, hydroxy(lower)alkyl, aryl(lower)alkyloxy (lower)alkyl, amino(lower)alkyl, (lower)alkanoylamino (lower)alkyl, or (lower)alkoxycarbonylamino(lower)alkyl, and
$R^2$ is hydrogen, aryl(lower)alkyl, lower alkanoyl or lower alkoxycarbonyl, or
$R^1$ and $R^2$ are bonded together and form lower alkylene;
$R^3$ and $R^5$ are independently amino, lower alkanoylamino or lower alkoxycarbonylamino; and
$R^4$ is carboxy or lower alkoxycarbonyl,
or a pharmaceutically acceptable salt thereof.

(3) The compound of (2) above wherein
$R^1$ is $(C_1-C_6)$alkyl, hydroxy$(C_1-C_6)$alkyl, mono-, di- or triphenyl-$(C_1-C_6)$alkyloxy$(C_1-C_6)$alkyl, amino$(C_1-C_6)$alkyl, $(C_1-C_6)$alkanoylamino$(C_1-C_6)$alkyl, or $(C_1-C_6)$alkoxycarbonylamino$(C_1-C_6)$alkyl, and
$R^2$ is hydrogen, mono-, di- or triphenyl$(C_1-C_6)$alkyloxy $(C_1-C_6)$alkyl, $(C_1-C_6)$alkanoyl or $(C_1-C_6)$alkoxycarbonyl, or
$R^1$ and $R^2$ are bonded together and form $(C_1-C_6)$alkylene;
$R^3$ and $R^5$ are independently amino, $(C_1-C_6)$alkanoylamino or $(C_1-C_6)$alkoxycarbonylamino; and
$R^4$ is carboxy or $(C_1-C_6)$alkoxycarbonyl,
or a pharmaceutically acceptable salt thereof.

(4) The compound of (2) above wherein
$R^1$ is lower alkyl, hydroxy(lower)alkyl or amino(lower)alkyl, and
$R^2$ is hydrogen, or
$R^1$ and $R^2$ are bonded together and form lower alkylene;
$R^3$ and $R^5$ are amino; and
$R^4$ is carboxy,
or a pharmaceutically acceptable salt thereof.

(5) The compound of (4) above wherein
$R^1$ is $(C_1-C_6)$alkyl, hydroxy$(C_1-C_6)$alkyl or amino$(C_1-C_6)$alkyl, and
$R^2$ is hydrogen, or
$R^1$ and $R^2$ are bonded together and form $(C_1-C_6)$alkylene;
$R^3$ and $R^5$ are amino; and
$R^4$ is carboxy,
or a pharmaceutically acceptable salt thereof.

The processes for preparing the object compound of the present invention are explained in detail in the following.

Process 1

The compound [I] or a salt thereof can be prepared by reacting the compound [II] or its reactive derivative at the amino group, or a salt thereof with the compound [III] or its reactive derivative at the carboxy group, or a salt thereof.

Suitable reactive derivative at the amino group of the compound [II] includes Schiff's base type imino or its tautomeric enamine type isomer formed by the reaction of the compound [II] with a carbonyl compound such as aldehyde, ketone and the like; a silyl derivative formed by the reaction of the compound [II] with a silyl compound such as bis(trimethylsilyl)acetamide, mono(trimethylsilyl) acetamide [e.g., N-(trimethylsilyl)acetamide], bis(trimethylsilyl)urea and the like; a derivative formed by the reaction of the compound [II] with phosphorus trichloride or phosgene.

Suitable salts of the compound [II] and its reactive derivative can be referred to the ones as exemplified for the compound [I].

Suitable reactive derivative at the carboxy group of the compound [III] includes an acid halide, an acid anhydride, an activated amide, and an activated ester. A suitable example of the reactive derivatives may be an acid chloride; an acid azide; a mixed acid anhydride with an acid such as substituted phosphoric acid [e.g., dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, alkanesulfonic acid [e.g., methanesulfonic acid, etc.], aliphatic carboxylic acid [e.g., acetic acid, propionic acid, butyric acid, isobutyric acid, pivalic acid, pentanoic acid, isopentanoic acid, 2-ethylbutyric acid, trichloroacetic acid, etc.] and aromatic carboxylic acid [e.g., benzoic acid, etc.]; a symmetrical acid anhydride; an activated amide with imidazole, 4-substituted imidazole, dimethylpyrazole, triazole or tetrazole; an activated ester [e.g., cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.]; or an ester with an N-hydroxy compound [e.g., N,N-dimethylhydroxylamine, 1-hydroxy-2-(1H)-pyridone, N-hydroxysuccinimide, N-hydroxyphthalimide, N-hydroxy-1H-benzotriazole, etc.]. These reactive derivatives can optionally be selected from them according to the kind of the compound [III] to be used.

Suitable salts of the compound [III] and its reactive derivative can be referred to the ones as exemplified for the compound [I].

The reaction is usually carried out in a conventional solvent such as water, alcohol [e.g., methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely affect the reaction. These conventional solvents may also be used in a mixture with water.

In this reaction, when the compound [III] is used in free acid form or its salt form, the reaction is preferably carried out in the presence of a conventional condensing agent such as N,N'-dicyclohexylcarbodiimide; N-cyclohexyl-N'-morpholinoethyl-carbodiimide; N-cyclohexyl-N'-(4-diethylaminocyclohexyl)-carbodiimide; N,N'-diethylcarbodiimide; N,N'-diisopropylcarbodiimide; N-ethyl-N'-(3-dimethylaminopropyl)carbodiimide; N,N'-carbonyl-bis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g., ethyl chloroformate, isopropyl chloroformate, etc.], triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; and the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, and the like.

The reaction temperature is not critical, and the reaction is usually carried out under cooling to warming.

Process 2

The compound [Ib] or a salt thereof can be prepared by subjecting the compound [Ia] or a salt thereof to elimination reaction of the amino protecting group.

Elimination reaction is carried out in accordance with a conventional method such as hydrolysis and the like.

The hydrolysis is preferably carried out in the presence of a base or an acid including Lewis acid.

Suitable base includes an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine (e.g., trimethylamine, triethylamine, etc.), picoline, 1,5-diazabicyclo[4.3.0]non-5-ene, 1,4-diazabicyclo[2.2.2]octane, 1,8-diazabicyclo[5.4.0]undec-7-ene, and the like.

Suitable acid includes an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.], and the like is preferably carried out in the presence of cation trapping agents [e.g., anisole, phenol, etc.].

The reaction is usually carried out in a solvent such as water, alcohol [e.g., methanol, ethanol, etc.], methylene chloride, tetrahydrofuran, a mixture thereof or any other solvent which does not adversely influence the reaction. A liquid base or acid can be also used as a solvent.

The reaction temperature is not critical and the reaction is usually carried out under cooling to warming.

Process 3-(i)

The compound [VIII] or a salt thereof can be prepared by reacting the compound [VI] or a salt thereof with the compound [VII] or a salt thereof.

Suitable salt of the compounds [VI] and [VIII] can be referred to the ones as exemplified for the compound [I].

The present reaction may be carried out in a solvent such as water, phosphate buffer, acetone, chloroform, acetonitrile nitrobenzene, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction, preferably in ones having strong polarities. Among the solvents, hydrophilic solvents may be used in a mixture with water. When the compound [VII] is liquid, it can also be used as a solvent.

The reaction is preferably conducted in the presence of a base, for example, an inorganic base such as alkali metal hydroxide, alkali metal carbonate, alkali metal hydrogencarbonate, an organic base such as trialkylamine, and the like.

The reaction temperature is not critical, and the reaction is usually carried out at ambient temperature, under warming or under heating. The present reaction is preferably carried out in the presence of alkali metal halide [e.g., sodium iodide, potassium iodide, etc.], alkali metal thiocyanate [e.g., sodium thiocyanate, potassium thiocyanate, etc.], and the like.

Anion X may be one derived from a leaving group Y, and it may be converted to other anion by a conventional method.

Process 3-(ii)

The compound [I] or a salt thereof can be prepared by subjecting the compound [VIII] or a salt thereof to elimination reaction of the carboxy protecting group.

Elimination reaction is carried out in similar manner to the reaction in the aforementioned Process 2, and therefore the reagents to be used and reaction conditions (e.g., solvent, reaction temperature, etc.) can be referred to those of Process 2.

Process 4

The compound [Id] or a salt thereof can be prepared by subjecting the compound [Ic] or a salt thereof to elimination reaction of the hydroxy protecting group or the amino protecting group.

Suitable method of this elimination reaction includes conventional one such as hydrolysis, reduction and the like.

(i) For hydrolysis:

The hydrolysis is preferably carried out in the presence of a base or an acid including Lewis acid.

Suitable base includes an inorganic base and an organic base such as an alkali metal [e.g., sodium, potassium, etc.], an alkaline earth metal [e.g., magnesium, calcium, etc.], the hydroxide or carbonate or hydrogencarbonate thereof, trialkylamine [e.g., trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, and the like.

Suitable acid includes an organic acid [e.g., formic acid, acetic acid, propionic acid, trichloroacetic acid, trifluoroacetic acid, etc.], and an inorganic acid [e.g., hydrochloric acid, hydrobromic acid, sulfuric acid, hydrogen chloride, hydrogen bromide, etc.].

The elimination using Lewis acid such as trihaloacetic acid [e.g., trichloroacetic acid, trifluoroacetic acid, etc.] and the like is preferably carried out in the presence of cation trapping agents [e.g., anisole, phenol, etc.].

The reaction is usually carried out in a solvent such as water, alcohol [e.g., methanol, ethanol, etc.], methylene chloride, tetrahydrofuran, a mixture thereof or any other solvent which does not adversely influence the reaction. A liquid base or acid can be also used as a solvent.

The reaction temperature is not critical and the reaction is usually carried out under cooling to warming.

(ii) For reduction:

Reduction is carried out in a conventional manner, including chemical reduction and catalytic reduction.

Suitable reducing reagents to be used in chemical reduction are a combination of a metal [e.g., tin, zinc, iron, etc.] or metallic compound [e.g., chromium chloride, chromium acetate, etc.] and an organic acid or inorganic acid [e.g., formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g., platinum plate, spongy platinum, platinum black, colloidal platinum, platinum oxide, platinum wire, etc.], palladium catalysts [e.g., spongy palladium, palladium black, palladium oxide, palladium on carbon, colloidal palladium, palladium on barium sulfate, palladium on barium carbonate, etc.], nickel catalysts [e.g., reduced nickel, nickel oxide, Raney nickel, etc.], cobalt catalysts [e.g., reduced cobalt, Raney cobalt, etc.], iron catalysts [e.g., reduced iron, Raney iron, etc.], copper catalysts [e.g., reduced copper, Raney copper, Ullman copper, etc.] and the like.

The reduction is usually carried out in a conventional solvent which does not adversely influence the reaction such as water, methanol, ethanol, propanol, N,N-dimethylformamide or a mixture thereof.

Additionally, in case that the above-mentioned acids to be used in chemical reduction are liquid, they can also be used as a solvent.

Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

When $R^5$ is protected amino, the amino protecting group in $R^5$ can be eliminated by a conventional method such as hydrolysis.

Processes A and B for the preparation of the starting compounds are explained in detail in the following.

Process A-(i)

The compound [XII] or a salt thereof can be prepared by reacting the compound [X] or a salt thereof with the compound [XI] or a salt thereof.

This reaction can be carried out in a similar manner to the reaction in the aforementioned Process 3-(i), and therefore the reagents to be used and reaction conditions (e.g., solvent, reaction temperature, etc.) can be referred to those of Process 3-(i).

Process A-(ii)

The compound [II] or a salt thereof can be prepared by subjecting the compound [XII] or a salt thereof to elimination reaction of the amino protecting groups in $R^8$ and $R^{10}$ and the carboxy protecting group in $R^9$.

This reaction can be carried out in a similar manner to the reaction in the aforementioned Process 2, and therefore the reagents to be used and reaction conditions (e.g., solvent, reaction temperature, etc.) can be referred to those of Process 2.

Process B

The compound [VI] or a salt thereof can be prepared by reacting the compound [XIII] or its reactive derivative at the amino group, or a salt thereof with the compound [XIV] or its reactive derivative at the carboxy group, or a salt thereof.

This reaction can be carried out in a similar manner to the reaction in the aforementioned Process 1, and therefore the reagents to be used and reaction conditions (e.g., solvent, reaction temperature, etc.) can be referred to those of Process 1.

The compounds obtained by the above processes can be isolated and purified by a conventional method such as pulverization, recrystallization, column chromatography, reprecipitation, and the like.

It is to be noted that the compound [I] and other compounds may include one or more stereoisomer(s) such as optical isomer(s) and geometrical isomer(s) due to asymmetric carbon atom(s) and double bond(s), and all of such isomers and mixtures thereof are included within the scope of this invention.

The object compounds [I] and pharmaceutically acceptable salts thereof include solvates [e.g., enclosure compounds (e.g., hydrate, etc.)].

The object compound [I] and pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compound [I], the test data on MIC (minimal inhibitory concentration) of a representative compound of this invention are shown in the following.

Test Method:

In vitro antibacterial activity was determined by the two-fold agar-plate dilution method as described below.

One loopful of an overnight culture of each test strain in Trypticase-soy broth ($10^6$ viable cells per ml) was streaked-on heart infusion agar (HI-agar) containing graded concentrations of representative test compound, and the minimal inhibitory concentration (MIC) was expressed in μg/ml after incubation at 37° C. for 20 hours.

Test Compound

Compound (a): 7β-[(Z)-2-(5-amino-1,2,4-thiadiazol-3-yl)-2-(1-carboxy-1-methylethoxyimino)acetamido]-3-[3-amino-4-(3-aminopropyl)-2-methyl-1-pyrazolio]methyl-3-cephem-4-carboxylate Compound (b): 7β-[(Z)-2-(5-amino-1,2,4-thiadiazol-3-yl)-2-(1-carboxy-1-methylethoxyimino)acetamido]-3-[3-amino-4-(2-aminoethyl)-2-methyl-1-pyrazolio]methyl-3-cephem-4-carboxylate Test Results:

TABLE 1

| Test strain | Test compound | MIC (μg/ml) |
|---|---|---|
| Pseudomonas aeruginosa | (a) | 1 |
| FP 2056 | (b) | 0.5 |

For therapeutic administration, the object compound [I] and pharmaceutically acceptable salts thereof of the present invention are used in the form of a conventional pharmaceutical preparation which contains said compound as an active ingredient, in admixture with pharmaceutically acceptable carriers such as an organic or inorganic solid or liquid excipient which is suitable for oral, parenteral or external administration. The pharmaceutical preparations may be in a solid form such as tablet, granule, powder, capsule, or in a liquid form such as solution, suspension, syrup, emulsion, lemonade and the like.

If needed, there may be included in the above preparations auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound [I] may very from and also depend upon the age, conditions of the patient, a kind of diseases, a kind of the compound [I] to be applied, etc. In general amounts between 1 mg and 4,000 mg or even more per day may be administered to a patient. An average single dose of about 50 mg, 100 mg, 250 mg, 500 mg, 1000 mg or 2000 mg of the object compounds [I] of the present invention may be used in treating diseases infected by pathogenic microorganisms.

The following Preparations and Examples are given for the purpose of illustrating the present invention in more detail.

Preparation 1

To a suspension of 5-amino-1-methylpyrazole-4-carbaldehyde (25 g, 200 mmol) and triethylamine (22.2 g, 220 mmol) in dichloromethane (500 ml) was added triphenylmethyl chloride (61.3 g, 220 mmol) at room temperature. The mixture was stirred at room temperature for 70 hours. The reaction mixture was washed with successively 10% aqueous citric acid solution, brine and 10% aqueous sodium hydrogencarbonate solution. The extract was dried over anhydrous magnesium sulfate, filtered, and concentrated in vacuo. The residue was triturated with ethyl acetate to give 1-methyl-5-triphenylmethylaminopyrazole-4-carbaldehyde (67.6 g) as a colorless solid.

$^1$H-NMR(CDCl$_3$) δ2.84 (3H, s), 7.26–7.34 (15H, m), 7.60 (1H, s), 8.95 (1H, brs), 9.58 (1H, s)

Preparation 2

To a suspension of sodium hydride (60% dispersion in mineral oil, 4.8 g, 120 mmol) in tetrahydrofuran (200 ml) was added dropwise triethyl phosphonoacetate (26.9 g, 120 mmol) under ice-cooling. The mixture was stirred under ice-cooling for 1 hour. To the reaction mixture was added 1-methyl-5-triphenylmethylaminopyrazole-4-carbaldehyde (36.7 g, 100 mmol) at room temperature, and the mixture was stirred at room temperature for 17 hours. After evaporation of the solvent in vacuo, the residue was dissolved in chloroform. The solution was washed with successively 10% aqueous citric acid solution, brine, and 10% aqueous sodium carbonate solution. The extract was dried over anhydrous magnesium sulfate, filtered, and concentrated in vacuo. The residue was triturated with ethyl acetate and dried in vacuo to give ethyl (E)-3-(1-methyl-5-triphenylmethylaminopyrazol-4-yl)acrylate (33.0 g) as a colorless solid.

$^1$H-NMR(CDCl$_3$) δ1.22 (3H, t, J=7.3 Hz), 3.07 (3H, s), 4.10 (2H, q, J=7.3 Hz), 5.78 (1H, d, J=16.0 Hz), 6.97 (1H, d, J=16.0 Hz), 7.19–7.33 (15H, m), 7.48 (1H, s)

Preparation 3

To a suspension of lithium aluminum hydride (5.7 g, 150 mmol) in tetrahydrofuran (200 ml) was added ethyl (E)-3-(1-methyl-5-triphenylmethylaminopyrazol-4-yl)acrylate (21.9 g, 50 mmol) at room temperature. The mixture was stirred at room temperature for 1 hour. After cooling on an ice bath, potassium fluoride (34 g) and water (10 ml) were added to the reaction mixture. The insoluble materials were removed by filtration. The filtrate was concentrated in vacuo, and the residue was dissolved in chloroform. The solution was washed with 10% aqueous citric acid solution. The organic layer was dried over anhydrous magnesium sulfate, filtered, and concentrated in vacuo. The oily residue was purified by column chromatography on silica gel eluting with chloroform to give 3-(1-methyl-5-triphenylmethylaminopyrazol-4-yl)propanol (14.8 g) as a solid.

$^1$H-NMR(CDCl$_3$) δ1.37–1.42 (2H, m), 1.87–1.90 (2H, m), 2.83 (3H, s), 3.38–3.42 (2H, m), 4.26 (1H, br), 7.12 (1H, s), 7.17–7.26 (15H, m)

Preparation 4

To a solution of 3-(1-methyl-5-triphenylmethylaminopyrazol-4-yl)propanol (4.0 g, 10 mmol), phthalimide (1.5 g, 10 mmol) and triphenylphosphine (4.0 g, 15 mmol) in tetrahydrofuran (20 ml) was added diisopropyl azodicarboxylate (3.0 g, 15 mmol), and the mixture was stirred at room temperature for 30 minutes. To the reaction mixture was added 4 mol/l hydrogen chloride solution in dioxane (10 ml), and the mixture was stirred at room temperature for 30 minutes. To the reaction mixture was added water, and the mixture was washed with ethyl acetate. The organic layer was separated, and the aqueous layer was adjusted to pH 9 with 10% aqueous sodium carbonate solution. The solution was extracted with chloroform. The organic layer was dried over anhydrous magnesium sulfate, filtered, and concentrated in vacuo. The residue was triturated with ethyl acetate and dried in vacuo to give 5-amino-1-methyl-4-(3-phthalimidopropyl)pyrazole (2.2 g) as a solid.

$^1$H-NMR(CDCl$_3$) δ1.91–1.97 (2H, m), 2.34–2.37 (2H, m), 3.45 (2H, br), 3.63 (3H, s), 3.71–3.77 (2H, m), 7.16 (1H, s), 7.70–7.73 (2H, m), 7.82–7.85 (2H, m)

Preparation 5

5-Amino-1-methyl-4-(3-phthalimidopropyl)pyrazole (1.42 g, 5 mmol) was added to concentrated hydrochloric acid (10 ml) at room temperature, and the mixture was stirred under reflux for 23 hours. To the reaction mixture was added water (50 ml), and most of insoluble materials were removed by filtration. The filtrate was washed with ethyl acetate, and the aqueous layer was concentrated in vacuo.

The residue was triturated with 2-propanol and dried in vacuo to give 3-(5-amino-1-methylpyrazol-4-yl)propylamine dihydrochloride (700 mg) as a solid.

$^1$H-NMR(DMSO-d$_6$) δ1.74–1.80 (2H, m), 2.44–2.47 (2H, m), 2.74–2.78 (2H, m), 3.73 (3H, s), 7.89 (1H, s), 8.25 (2H, br)

Preparation 6

To a solution of 3-(5-amino-1-methylpyrazol-4-yl)propylamine dihydrochloride (9.3 g, 40 mmol) in methanol (80 ml) was added 28% sodium methoxide solution in methanol (15.9 g). The mixture was filtered through Celite, and the filtrate was concentrated in vacuo. A solution of the oily residue in ethyl formate (60 g) was stirred under reflux for 20 hours. After cooling, to the reaction mixture was added chloroform. The mixture was filtered through Celite, and the filtrate was concentrated in vacuo. The residue was triturated with ethyl acetate and dried in vacuo to give N-[3-(5-amino-1-methylpyrazol-4-yl)propyl]formamide (6.7 g) as a solid.

$^1$H-NMR(DMSO-d$_6$) δ1.74–1.80 (2H, m), 2.44–2.47 (2H, m), 2.74–2.78 (2H, m), 3.73 (3H, s), 7.89 (1H, s), 8.25 (2H, br)

Preparation 7

To a solution of N-[3-(5-amino-1-methylpyrazol-4-yl) propyl]formamide (3.64 g, 20 mmol) and triethylamine (2.23 g, 22 mmol) in methylene chloride (50 ml) was added triphenylmethyl chloride (6.13 g, 22 mmol). The mixture was stirred at room temperature for 90 minutes. The reaction mixture was washed with successively 10% aqueous citric acid solution, brine, and 10% aqueous sodium carbonate solution. The organic layer was dried over anhydrous magnesium sulfate, filtered, and concentrated in vacuo. The residue was triturated with ethyl acetate and dried in vacuo to give N-[3-(1-methyl-5-triphenylmethylaminopyrazol-4-yl)propyl]formamide (6.8 g) as a solid.

$^1$H-NMR(DMSO-d$_6$) δ1.13–1.18 (2H, m), 1.79–1.82 (2H, m), 2.76 (3H, s), 2.79–2.83 (2H, m), 5.68 (1H, s), 7.01 (1H, s), 7.15–7.27 (15H, m), 7.81 (1H, br), 7.96 (1H, s)

Preparation 8

To a solution of benzhydryl 7β-tert-butoxycarbonylamino-3-chloromethyl-3-cephem-4-carboxylate (1.03 g, 2.00 mmol) in N,N-dimethylformamide (2.5 ml) was added sodium iodide (300 mg, 2.00 mmol), and the mixture was stirred at room temperature for 30 minutes. To the reaction mixture were added N-[3-(1-methyl-5-triphenylmethylaminopyrazol-4-yl)propyl]formamide (2.55 g, 6.00 mmol) and methylene chloride (5 ml). The whole mixture was stirred at room temperature for 18 hours and poured into a mixture of ethyl acetate and water. The aqueous layer was separated, and the organic layer was washed with brine, dried over sodium sulfate and filtered. The filtrate was concentrated to about 20 ml in vacuo. The concentrate was poured into diisopropyl ether (300 ml), and the resulting precipitate was collected by filtration and dried in vacuo. To a solution of the resulting solid in methylene chloride (7.5 ml) were added anisole (2.5 ml) and trifluoroacetic acid (5.0 ml) under ice-cooling. The resulting solution was stirred at room temperature for 3 hours and poured into diisopropyl ether (300 ml). The resulting precipitate was collected by filtration and dried in vacuo to give crude 7β-amino-3-[3-amino-4-(3-formamidopropyl)-2-methyl-1-pyrazolio]methyl-3-cephem-4-carboxylate bistrifluoroacetic acid salt (1.67 g). This product was used in the next step without further purification.

EXAMPLE 1

To a solution of crude 7β-amino-3-[3-amino-4-(3-formamidopropyl)-2-methyl-1-pyrazolio]methyl-3-cephem-4-carboxylate bistrifluoroacetic acid salt (1.65 g) and N-trimethylsilylacetamide (2.94 g, 22.4 mmol) in a mixed solvent of N,N-dimethylformamide (16 ml) and tetrahydrofuran (16 ml) was added (Z)-2-(5-amino-1,2,4-thiadiazol-3-yl)-2-(1-tert-butoxycarbonyl-1-methylethoxyimino)acetyl chloride hydrochloride salt (863 mg, 2.24 mmol) under ice-cooling. The solution was stirred under ice-cooling for 2.5 hours. The reaction mixture was poured into ethyl acetate (400 ml), and the mixture was stirred for 30 minutes. The resulting precipitate was collected by filtration, washed with successively ethyl acetate and diisopropyl ether, and dried in vacuo to give a solid (1.07 g).

To a suspension of the resulting solid in methylene chloride (3.0 ml) were added anisole (1.0 ml) and trifluoroacetic acid (2.0 ml) under ice-cooling. The resulting solution was stirred at room temperature for 2.5 hours and poured into diisopropyl ether (150 ml). The resulting precipitate was collected by filtration and dried in vacuo to give a crude product, which was purified by preparative high-performance liquid chromatography (HPLC) utilizing ODS column. The eluate containing a desired product was concentrated to about 30 ml in vacuo. The concentrate was adjusted to about pH 3 with concentrated hydrochloric acid and chromatographed on microporous non-ionic adsorption resin Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)acetamido]-3-[3-amino-4-(3-formamidopropyl)-2-methyl-1-pyrazolio]methyl-3-cephem-4-carboxylate (118 mg) as an amorphous solid.

$^1$H-NMR(D$_2$O) δ1.52 (3H, s), 1.53 (3H, s), 1.80 (2H, quintet, J=7.0 Hz), 2.43 (2H, t, J=7.0 Hz), 3.13 and 3.30 (2H, ABq, J=17.5 Hz), 3.25 (2H, t, J=7.0 Hz), 3.67 (3H, s), 4.96 and 5.22 (2H, ABq, J=15.8 Hz), 5.22 (1H, d, J=4.8 Hz), 5.85 (1H, d, J=4.8 Hz), 7.77 (1H, s), 8.04 (1H, s)

EXAMPLE 2

To a solution of 7β-[(Z)-2-(5-amino-1,2,4-thiadiazol-3-yl)-2-(1-carboxy-1-methylethoxyimino)acetamido]-3-[3-amino-4-(3-formamidopropyl)-2-methyl-1-pyrazolio] methyl-3-cephem-4-carboxylate (112 mg, 0.172 mmol) in methanol (1.1 ml) was added concentrated hydrochloric acid (0.11 ml) at room temperature. The mixture was stirred at room temperature for 4 hours. The reaction mixture was adjusted to about pH 6 with saturated aqueous sodium hydrogencarbonate solution and concentrated in vacuo to remove methanol. The resulting residue was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)-acetamido]-3-[3-amino-4-(3-aminopropyl)-2-methyl-1-pyrazolio]methyl-3-cephem-4-carboxylate (20 mg) as an amorphous solid.

$^1$H-NMR(D$_2$O) δ1.53 (3H, s), 1.54 (3H, s), 1.93 (2H, quintet, J=7.5 Hz), 2.49 (2H, t, J=7.5 Hz), 3.02 (2H, t, J=7.5 Hz), 3.16 and 3.38 (2H, ABq, J=17.3 Hz), 3.69(3H, s), 4.93 and 5.16 (2H, ABq, J=15.3 Hz), 5.24 (1H, d, J=4.8 Hz), 5.84 (1H, d, J=4.8 Hz), 7.78 (1H, s)

Preparation 9

A solution of ethyl (E)-3-(1-methyl-5-triphenylmethylaminopyrazol-4-yl)acrylate (60 g, 137 mmol) in ethanol (700 ml) was treated with 10% palladium carbon (6.0 g) under a hydrogen atmosphere at room temperature for 3 hours. After the catalyst was filtered off, the filtrate was concentrated in vacuo. The residue was triturated with hexane and dried in vacuo to give ethyl 3-(1-methyl-5-triphenylmethylaminopyrazol-4-yl)propionate (63 g) as a colorless solid.

$^1$H-NMR(CDCl$_3$) δ1.21 (3H, t, J=7.3 Hz), 2.09–2.16 (4H, m), 2.81 (3H, s), 4.07 (2H, q, J=7.3 Hz), 4.61 (1H, s), 7.11 (1H, s), 7.19–7.28 (15H, m)

Preparation 10

To a solution of ethyl 3-(1-methyl-5-triphenylmethylaminopyrazol-4-yl)propionate (22 g, 50 mmol) in methanol (60 ml) was added 10% aqueous sodium hydroxide solution (60 ml), and the mixture was stirred under reflux for 2 hours. The reaction mixture was acidified with 10% aqueous citric acid solution, and the mixture was extracted with a mixed solvent of chloroform and methanol. The extract was dried over anhydrous magnesium sulfate, filtered, and concentrated in vacuo. The residue was triturated with diisopropyl ether and dried in vacuo to give 3-(1-methyl-5-triphenylmethylaminopyrazol-4-yl)propionic acid (16 g) as a colorless solid.

$^1$H-NMR(DMSO-d$_6$) δ1.88 (2H, t, J=7.8 Hz), 2.08 (2H, t, J=7.8 Hz), 2.75 (3H, s), 5.75 (1H, s), 6.99 (1H, s), 7.15–7.26 (15H, m), 11.85 (1H, br)

Preparation 11

To a solution of 3-(1-methyl-5-triphenylmethylaminopyrazol-4-yl)propionic acid (14.4 g, 35 mmol) and triethylamine (4.9 ml, 35 mmol) in tetrahydrofuran (150 ml) was added ethyl chloroformate (3.4 ml, 35 mmol) followed by stirring for 20 minutes under ice-cooling. To the reaction mixture was added a solution of sodium azide (2.3 g, 35 mmol) in water (30 ml) under ice-cooling. The mixture was stirred under ice-cooling for 20 minutes and then at room temperature for 20 minutes. To the reaction mixture was added ice-cold water, and the mixture was extracted with ethyl acetate. The extract was washed with saturated aqueous sodium hydrogencarbonate solution, dried over anhydrous magnesium sulfate, and filtered. To the filtrate was added methanol, and the mixed solution was concentrated in vacuo. To the residue was added methanol (150 ml), and the mixture was stirred under reflux for 1.5 hours. The reaction mixture was concentrated in vacuo to give methyl N-[2-(1-methyl-5-triphenylmethylaminopyrazol-4-yl)ethyl]carbamate (15.6 g) as a colorless solid.

$^1$H-NMR(CDCl$_3$) δ2.00 (2H, t, J=7.3 Hz), 2.85 (3H, s), 2.87 (2H, t, J=7.3 Hz), 3.64 (3H, s), 4.16 (1H, br), 4.36 (1H, br), 7.15–7.29 (16H, m)

Preparation 12

A mixture of methyl N-[2-(1-methyl-5-triphenylmethylaminopyrazol-4-yl)ethyl]carbamate (15.3 g, 34.7 mmol) and concentrated hydrochloric acid (80 ml) was stirred under reflux for 13 hours. The reaction mixture was washed with ethyl acetate. The organic layer was separated, and the aqueous layer was concentrated in vacuo. The residue was triturated with diisopropyl ether and dried in vacuo to give 2-(5-amino-1-methylpyrazol-4-yl)ethylamine dihydrochloride (6.1 g) as a colorless solid.

$^1$H-NMR(DMSO-d$_6$) δ2.68–2.71 (2H, m), 2.91–2.95 (2H, m), 3.69 (3H, s), 7.82 (1H, s), 8.14 (2H, br)

Preparation 13

To a solution of 2-(5-amino-1-methylpyrazol-4-yl)ethylamine dihydrochloride (2.98 g, 14 mmol) in methanol (50 ml) was added 28% sodium methoxide solution in methanol (5.4 ml, 28 mmol). The mixture was filtered through Celite, and the filtrate was concentrated in vacuo. A mixture of the residue and ethyl formate (80 ml) was stirred under reflux for 16 hours. To the reaction mixture was added chloroform, and the mixture was filtered through Celite. The filtrate was concentrated in vacuo to give N-[2-(5-amino-1-methylpyrazol-4-yl)ethyl]formamide (2.7 g) as a brown oil. $^1$H-NMR (CDCl$_3$) δ2.57 (2H, t, J=6.9 Hz), 3.40–3.44 (2H, m), 3.67 (3H, s), 5.77 (1H, br), 7.15 (1H, s), 8.16 (1H, s)

Preparation 14

To a solution of N-[2-(5-amino-1-methylpyrazol-4-yl) ethyl]formamide (2.7 g, 16 mmol) and triethylamine (2.5 ml, 17.6 mmol) in methylene chloride (50 ml) was added triphenylmethyl chloride (5.2 g, 17.6 mmol), and the mixture was stirred at room temperature for 3 hours. The reaction mixture was washed with successively 10% aqueous citric acid solution and brine. The organic layer was dried over anhydrous magnesium sulfate, filtered, and concentrated in vacuo. The residue was triturated with diisopropyl ether and dried in vacuo to give N-[2-(1-methyl-5-triphenylmethylaminopyrazol-4-yl)ethyl]formamide (4.7 g) as a colorless solid.

$^1$H-NMR(CDCl$_3$) δ2.04 (2H, t, J=6.9 Hz), 2.87 (3H, s), 3.01–3.06 (2H, m), 4.19 (1H, br), 5.17 (1H, br), 7.14–7.31 (16H, m), 8.02 (1H, s)

Preparation 15

7β-Amino-3-[3-amino-4-(2-formamidoethyl)-2-methyl-1-pyrazolio]methyl-3-cephem-4-carboxylate bistrifluoroacetic acid salt The title-compound was obtained from benzhydryl 7β-tert-butoxycarbonylamino-3-chloromethyl-3-cephem-4-carboxylate and N-[2-(1-methyl-5-triphenylmethylaminopyrazol-4-yl)ethyl]formamide in the same manner as in Preparation 8.

EXAMPLE 3

7β-[(Z)-2-(5-Amino-1,2,4-thiadiazol-3-yl)-2-(1-carboxy-1-methylethoxyimino)acetamido]-3-[3-amino-4-(2-formamidoethyl)-2-methyl-1-pyrazolio]methyl-3-cephem-4-carboxylate The title compound was obtained from 7β-amino-3-[3-amino-4-(2-formamidoethyl)-2-methyl-1-pyrazolio]methyl-3-cephem-4-carboxylate bistrifluoroacetic acid salt and (Z)-2-(5-amino-1,2,4-thiadiazol-3-yl)-2-(1-tert-butoxycarbonyl-1-methylethoxyimino)acetyl chloride hydrochloride salt in the same manner as in Example 1.

$^1$H-NMR(D$_2$O) δ1.60 (3H, s), 1.62 (3H, s), 2.63 (2H, t, J=6.5 Hz), 3.12–3.30 (2H, ABq, J=17.5 Hz), 3.41 (1H, dt, J=13.3, 6.5 Hz), 3.45 (1H, dt, J=13.3, 6.5 Hz), 3.67 (3H, s), 4.96 and 5.22 (2H, ABq, J=16.0 Hz), 5.23 (1H, d, J=5.0 Hz), 5.86 (1H, d, J=5.0 Hz), 7.78 (1H, s), 8.02 (1H, s)

EXAMPLE 4

7β-[(Z)-2-(5-Amino-1,2,4-thiadiazol-3-yl)-2-(1-carboxy-1-methylethoxyimino)acetamido]-3-[3-amino-4-(2-aminoethyl)-2-methyl-1-pyrazolio]methyl-3-cephem-4-carboxylate The title compound was obtained from 7β-[(Z)-2-(5-Amino-1,2,4-thiadiazol-3-yl)-2-(1-carboxy-1-methyl-ethoxyimino)-acetamido]-3-[3-amino-4-(2-formamidoethyl)-2-methyl-1-pyrazolio]methyl-3-cephem-4-carboxylate in the same manner as in Example 2.

$^1$H-NMR(D$_2$O) δ1.53 (3H, s), 1.54 (3H, s), 2.81 (2H, t, J=7.5 Hz), 3.20 and 3.47 (2H, ABq, J=18.0 Hz), 3.21 (2H, t, J=7.5 Hz), 3.70 (3H, s), 4.95 and 5.15 (2H, ABq, J=15.5 Hz), 5.25 (1H, d, J=5.0 Hz), 5.84 (1H, d, J=5.0 Hz), 7.82 (1H, s)

Preparation 16

To a suspension of 5-amino-1-(2-hydroxyethyl)pyrazole-4-carbonitrile (10 g, 65.7 mmol) and pyridine (100 ml) was added triphenylmethyl chloride (22.3 g, 78.9 mmol) at room temperature. After stirring at 60° C. for 6 hours, the reaction mixture was concentrated in vacuo. To the residue were added tetrahydrofuran and brine, and the separated organic layer was washed with brine. The extract was dried over anhydrous magnesium sulfate, filtered, and concentrated in vacuo. The residue was triturated with ethyl acetate to give 5-amino-1-[2-(trityloxy)ethyl]pyrazole-4-carbonitrile (25.4 g) as a colorless solid.

$^1$H-NMR(DMSO-d$_6$) δ3.14 (2H, t, J=4.9 Hz), 4.16 (2H, t, J=4.9 Hz), 6.71 (2H, s), 7.21–7.38 (15H, m), 7.61 (1H, s)

Preparation 17

To a suspension of lithium aluminum hydride (4.89 g, 129 mmol) in tetrahydrofuran (318 ml) was added 5-amino-1-[2-(trityloxy)ethyl]pyrazole-4-carbonitrile (25.4 g, 64.4 mmol) at room temperature. The mixture was stirred under reflux for 12 hours. After cooling on an ice bath, sodium fluoride (25.4 g), tetrahydrofuran (100 ml), dichloromethane (200 ml) and water (10 ml) were added to the reaction mixture. The insoluble materials were removed by filtration. The filtrate was concentrated in vacuo to give {5-amino-1-[2-(trityloxy)ethyl]pyrazol-4-yl}methylamine (19.8 g) as a solid.

$^1$H-NMR(DMSO-d$_6$) δ3.16 (2H, t, J=5.5 Hz), 3.45 (2H, s), 4.10 (2H, t, J=5.5 Hz), 5.04 (2H, s), 7.04 (1H, s), 7.08–7.32 (15H, m)

Preparation 18

A suspension of {5-amino-1-[2-(trityloxy)ethyl]pyrazol-4-yl}methylamine (19.7 g, 49.4 mmol) in ethyl formate (500 ml) was stirred at 50° C. for 3 hours. After evaporation of the solvent in vacuo, the residue was triturated with diisopropyl ether to give N-{5-amino-1-[2-(trityloxy)ethyl]pyrazol-4-yl}methylformamide (7.99 g) as a solid.

$^1$H-NMR(DMSO-d$_6$) δ3.14 (2H, t, J=5.5 Hz), 3.99 (2H, d, J=5.8 Hz), 4.09 (2H, t, J=5.5 Hz), 5.21 (2H, s), 7.05 (1H, s), 7.18–7.32 (15H, m), 8.01 (1H, d, J=1.7 Hz), 8.25 (1H, m)

Preparation 19

To a solution of (Z)-2-(5-amino-1,2,4-thiadiazol-3-yl)[(2-tert-butoxy-1,1-dimethyl-2-oxoethoxy)imino]ethanoic acid (5 g) in a mixture of tetrahydrofuran (80 ml) and N,N-dimethylformamide (20 ml) was added a solution of sodium bis(trimethylsilyl)amide (8.33 g) in tetrahydrofuran (12 ml), and the mixture was stirred for 15 minutes. To the reaction mixture was added a solution of di-tert-butyl dicarbonate (3.3 g) in tetrahydrofuran (20 ml) under ice-cooling, and the mixture was stirred under ice-cooling for 3 hours. To the reaction mixture was added ethyl acetate, and the mixture was washed with 10% aqueous potassium hydrogensulfate solution, and then washed with a phosphate buffer (pH 6.86). The organic layer was separated, dried over anhydrous magnesium sulfate, filtered, and concentrated in vacuo. The residue was triturated with diisopropyl ether and dried in vacuo to give (Z)-2-{5-[(tert-butoxycarbonyl)amino]-1,2,4-thiadiazol-3-yl}[(2-tert-butoxy-1,1-dimethyl-2-oxoethoxy) imino]ethanoic acid (3.10 g).

$^1$H-NMR(DMSO-d$_6$) δ1.37 (9H, s), 1.45 (6H, s), 1.50 (9H, s), 12.7 (1H, s)

IR(KBr): 3191.6, 2981.4, 1714.4, 1550.5, 1153.2, 1000.9 cm$^{-1}$

ESI-MASS: m/z=429(M−H)

Preparation 20

A mixture of N,N-dimethylformamide (0.648 ml) and phosphoryl chloride (0.781 ml) was stirred at room temperature for 30 minutes. To the mixture were added tetrahydrofuran (4 ml) and (Z)-2-{5-[(tert-butoxy carbonyl)amino]-1,2,4-thiadiazol-3-yl}[(2-tert-butoxy-1,1-dimethyl-2-oxoethoxy)imino]ethanoic acid (3 g) at 4° C., and the reaction mixture was stirred at room temperature for 1 hour. Meanwhile, a mixture of benzhydryl 7β-amino-3-chloromethyl-3-cephem-4-carboxylate hydrochloride (3 g) and N-trimethylsilylacetamide (8.72 g) in tetrahydrofuran (15 ml) was warmed to make a clear solution. The solution was then cooled to −20° C. and added to the activated acid solution obtained above. The reaction mixture was stirred at a temperature of −10° C. to 0° C. for 1 hour and poured into a mixture of ethyl acetate and water. The aqueous layer was separated, and the organic layer was washed with brine, dried over anhydrous magnesium sulfate and filtered. The filtrate was concentrated in vacuo and purified by column chromatography on silica gel eluting with hexane/ethyl acetate (3:2) to give benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (4.79 g).

$^1$H-NMR(DMSO-d$_6$) δ1.39 (6H, s), 1.48 (3H, s), 1.50 (6H, s), 3.58 (1H, d, J=18.3 Hz), 3.76 (1H, d, J=18.3 Hz), 4.44 (2H, s), 5.29 (1H, d, J=5.0 Hz), 6.01 (1H, dd, J=8.6, 5.0 Hz), 6.97 (1H, s), 7.2–7.6 (10H, m), 9.65 (1H, d, J=5.0 Hz), 12.7 (1H, s)

IR(KBr): 2981.4, 1793.5, 1720.2, 1524.8, 1371.1, 1247.7, 1151.3 cm$^{-1}$

ESI-MASS: m/z=849 (M+Na)

EXAMPLE 5

To a solution of 5-amino-4-formamidomethyl-1-(2-triphenylmethyloxyethyl)pyrazole (2.06 g) in dichloromethane (10 ml) were added trimethylsilyl iodide (1.38 ml) and diisopropylethylamine (1.68 ml) under ice-cooling, and the mixture was stirred under ice-cooling for 2 hours. To the reaction mixture was added a mixture of benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (2 g) and sodium iodide (364 mg) in N,N-dimethylformamide (4 ml) which had been stirred under ice-cooling for 0.5 hour. The reaction mixture was stirred at room temperature for 22 hours and added to a mixture of ethyl acetate and water. The organic layer was separated and dried over magnesium sulfate. The magnesium sulfate was filtered off, and the filtrate was concentrated to about 20 ml in vacuo. The concentrate was poured into diisopropyl ether (150 ml), and the resulting precipitate was collected by filtration and dried in vacuo. To a solution of the resulting solid in methylene chloride (9 ml) were added anisole (3 ml) and trifluoroacetic acid (6 ml). The resulting solution was stirred at room temperature for 3 hours and poured into diisopropyl ether (300 ml). The resulting precipitate was collected by filtration and dried in vacuo. The obtained powder was dissolved in a phosphate buffer (pH 7), and the solution was adjusted to about pH 6 with saturated aqueous sodium hydrogencarbonate solution. The solution containing the objective compound was purified by preparative HPLC utilizing ODS column. The eluate containing a desired product was concentrated in vacuo. The concentrate was adjusted to about pH 2 with concentrated hydrochloric acid and chromatographed on Diaion® HP-20 (Mitsubishi Chemical Corporation) eluting with 20% aqueous 2-propanol. The eluate was evaporated in vacuo and lyophilized to give 7β-[(Z)-2-(5-amino-1,2,4-thiadiazol-3-yl)-2-(1-carboxy-1-methylethoxyimino)-acetamido]-3-[3-amino-4-formamidomethyl-2-(2-hydroxyethyl)-1-pyrazolio]methyl-3-cephem-4-carboxylate (103 mg) as an amorphous solid.

$^1$H-NMR($D_2O$) δ1.54 (3H, s), 1.55 (3H, s), 3.07 (1H, d, J=17.7 Hz), 3.36 (1H, d, J=17.7 Hz), 3.84 (2H, t, J=4.8 Hz), 4.23 (2H, s), 4.33 (2H, s), 4.33 (2H, t, J=4.8 Hz), 5.04 (1H, d, J=12.3 Hz), 5.16 (1H, d, J=12.3 Hz), 5.22 (1H, d, J=4.9 Hz), 5.85 (1H, d, J=4.9 Hz), 7.94 (1H, s), 8.11 (1H, s)

IR(KBr): 3318.9, 1772.3, 1666.2, 1652.7, 1396.2 $cm^{-1}$

ESI-MASS: m/z=651(M–H)$^+$

EXAMPLE 6

To a solution of 7β-[(Z)-2-(5-amino-1,2,4-thiadiazol-3-yl)-2-(1-carboxy-1-methylethoxyimino)acetamido]-3-[3-amino-4-formamidomethyl-2-(2-hydroxyethyl)-1-pyrazolio]methyl-3-cephem-4-carboxylate (97 mg) in methanol (1 ml) was added concentrated hydrochloric acid (0.1 ml) at room temperature. The mixture was stirred at room temperature for 4.5 hours and poured into ethyl acetate. The resulting precipitate was collected by filtration and dried in vacuo. The obtained powder was dissolved in a phosphate buffer (pH 7), and the solution was adjusted to about pH 6 with saturated aqueous sodium hydrogencarbonate solution. The solution containing the objective compound was purified by preparative HPLC utilizing ODS column. The eluate containing the desired product was concentrated in vacuo. The concentrate was adjusted to about pH 2 with concentrated hydrochloric acid and chromatographed on Diaion® HP-20 (Mitsubishi Chemical Corporation) eluting with 20% aqueous 2-propanol. The eluate was concentrated in vacuo and lyophilized to give 7β-[(Z)-2-(5-amino-1,2,4-thiadiazol-3-yl)-2-(1-carboxy-1-methylethoxyimino)acetamido]-3-[3-amino-4-aminomethyl-2-(2-hydroxyethyl)-1-pyrazolio]methyl-3-cephem-4-carboxylate (17.5 mg).

$^1$H-NMR($D_2O$) δ1.53 (3H, s), 1.54 (3H, s), 3.17 (1H, d, J=17.7 Hz), 3.53 (1H, d, J=17.7 Hz), 3.89 (2H, t, J=4.7 Hz), 4.10 (2H, s), 4.41 (2H, t, J=4.7 Hz), 5.04 (1H, d, J=17.6 Hz), 5.15 (1H, d, J=17.6 Hz), 5.28 (1H, d, J=4.9 Hz), 5.86 (1H, d, J=4.9 Hz), 8.10 (1H, s)

ESI-MASS: m/z=623(M–H)$^+$

Preparation 21

To a suspension of sodium hydride (55% dispersion in mineral oil, 26.2 g, 600 mmol) in tetrahydrofuran (1000 ml) was added diethyl(cyanomethyl)phosphonate (106.3 g, 600 mmol) under ice-cooling. The mixture was stirred under ice-cooling for 20 minutes. To the mixture was added 1-methyl-5-triphenylmethylaminopyrazole-4-carbaldehyde (197 g, 530 mmol), and the mixture was stirred for 2 hours. The reaction mixture was poured into ice-cold water. The mixture was extracted with ethyl acetate. The extract was dried over anhydrous magnesium sulfate, filtered, and concentrated in vacuo. The residue was triturated with diethyl ether to give 3-(1-methyl-5-triphenylmethylaminopyrazol-4-yl)acrylonitrile (E, Z mixture, 126 g) as a solid.

E Form
$^1$H-NMR(CDCl$_3$) δ3.14 (3H, s), 4.45 (1H, br), 5.09 (1H, d, J=16.5 Hz), 6.43 (1H, d, J=16.5 Hz), 7.17–7.32 (15H, m), 7.42 (1H, s)

Z Form
$^1$H-NMR(CDCl$_3$) δ3.09 (3H, s), 4.37 (1H, br), 4.58 (1H, d, J=11.9 Hz), 6.22 (1H, d, J=11.9 Hz), 7.17–7.32 (15H, m), 8.14 (1H, s)

Preparation 22

To a solution of 3-(1-methyl-5-triphenylmethylaminopyrazol-4-yl)acrylonitrile (E,Z mixture, 26 g, 66.6 mmol) in methylene chloride (250 ml) was added dropwise a solution of diisobutylaluminum hydride in toluene (1.0 mol/l, 200 ml, 200 mmol) under ice-cooling. The mixture was stirred at room temperature for 24 hours. To the reaction mixture was added dropwise methanol (100 ml). To the mixture were added sodium fluoride (5 g) and methanol (300 ml). The insoluble materials were removed by filtration. After evaporation of the solvent in vacuo, the oily residue was dissolved in methylene chloride. To the solution were added saturated aqueous sodium hydrogencarbonate solution (25 ml) and di-tert-butyl dicarbonate (20 g). The mixture was stirred at room temperature for 17 hours. The aqueous layer was separated, and the organic layer was washed with water. The organic layer was dried over sodium sulfate, filtered, and concentrated in vacuo. The residue was purified by column chromatography on silica gel eluting with ethyl acetate/hexane. The eluate was concentrated in vacuo, and the residue was recrystallized from diethyl ether to give tert-butyl N-[3-(1-methyl-5-triphenylmethylaminopyrazol-4-yl)-2-propenyl]carbamate (E,Z mixture, 1.8 g) as colorless crystals.

E Form
$^1$H-NMR(CDCl$_3$) δ1.47 (9H, s), 2.90 (3H, s), 3.49–3.52 (2H, m), 4.17 (1H, s), 4.18 (1H, br), 5.55–5.63 (2H, m), 7.18–7.30 (15H, m), 7.38 (1H, s)

Z Form
$^1$H-NMR(CDCl$_3$) δ1.44 (9H, s), 2.95 (3H, s), 3.76–3.80 (2H, m), 4.35 (1H, br), 4.38 (1H, br), 5.05–5.09 (1H, m), 5.56 (1H, d, J=11.5 Hz), 7.18–7.29 (16H, m)

EXAMPLE 7

To a solution of benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (1.02 g, 1.20 mmol) in N,N-dimethylformamide (2.1 ml) was added sodium iodide (203 mg, 1.35 mmol), and the mixture was stirred at room temperature for 30 minutes. To the resulting reaction mixture were added tert-butyl N-[3-(1-methyl-5-triphenylmethylaminopyrazol-4-yl)-2-propenyl]carbamate (E,Z mixture, 1.40 g, 2.80 mmol) and methylene chloride (4.2 ml). The whole mixture was stirred at room temperature for 24 hours. To the reaction mixture were added ethyl acetate (100 ml) and water (50 ml). The aqueous layer was separated, and the organic layer was washed with brine, dried over sodium sulfate, and filtered. The filtrate was concentrated to about 5 ml in vacuo. The concentrate was poured into diisopropyl ether (160 ml), and the resulting precipitate was collected by filtration and dried in vacuo. To a solution of the resulting solid in methylene chloride (4.29 ml) were added anisole (1.43 ml) and trifluoroacetic acid (2.86 ml) under ice-cooling. The resulting solution was stirred at room temperature for 3 hours and poured into diisopropyl ether (120 ml). The resulting precipitate was collected by filtration and dried in vacuo to give a solid (1.32 g). The solid was purified by preparative HPLC utilizing ODS column. The first eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)acetamido]-3-[3-amino-4-((E)-3-amino-1-propenyl)-2-methyl-1-pyrazolio]methyl-3-cephem-4-carboxylate (35 mg) as an amorphous solid.

$^1$H-NMR(D$_2$O) δ1.52 (6H, s), 3.18 and 3.44 (2H, ABq, J=17.8 Hz), 3.71 (3H, s), 3.73 (2H, d, J=7.0 Hz), 4.99 and 5.17 (2H, ABq, J=15.3 Hz), 5.25 (1H, d, J=4.8 Hz), 5.84 (1H, d, J=4.8 Hz), 6.08 (1H, dt, J=16.0, 7.0 Hz), 6.49 (1H, d, J=16.0 Hz), 8.05 (1H, s)

The second eluate was treated in the same manner as described above to give 7β-[(Z)-2-(5-amino-1,2,4-thiadiazol-3-yl)-2-(1-carboxy-1-methylethoxyimino)acetamido]-3-[3-amino-4-((Z)-3-amino-1-propenyl)-2-methyl-1-pyrazolio]methyl-3-cephem-4-carboxylate (14 mg) as an amorphous solid.

$^1$H-NMR(D$_2$O) δ1.52 (6H, s), 3.21 and 3.47 (2H, ABq, J=18.0 Hz), 3.72 (3H, s), 3.79 (1H, ddd, J=14.7, 6.7, 1.6 Hz), 3.82 (1H, ddd, J=14.7 Hz, 6.7 Hz, 1.6 Hz), 4.98 and 5.18 (2H, ABq, J=15.3 Hz), 5.25 (1H, d, J=5.0 Hz), 5.83 (1H, dt, J=11.5, 6.7 Hz), 5.84 (1H, d, J=5.0 Hz), 6.35 (1H, d, J=11.5 Hz), 7.91 (1H, s)

Preparation 23

To a solution of 5-amino-4-aminomethyl-1-methylpyrazole dihydrochloride (10 g) in methanol (100 ml) was added 28% sodium methoxide solution in methanol (19.4 ml). The mixture was filtered, and the filtrate was concentrated in vacuo. Separately, acetic anhydride (14.2 ml) was added to formic acid (11.5 ml), and the mixture was stirred at room temperature for 30 minutes. The resulting mixture was added to the oily residue obtained above (5-amino-4-aminomethyl-1-methylpyrazole), and the mixture was stirred at room temperature for 2 hours. After evaporation of the solvent in vacuo, water was added to the residue. The mixture was adjusted to pH 9.5 with Diaion® SA10A(OH$^-$) (Mitsubishi Chemical Coporation). The mixture was filtered and concentrated in vacuo. The residue was purified by column chromatography on silica gel eluting with dichloromethane/methanol (3:1) to give 5-formamido-4-formamidomethyl-1-methylpyrazole (3.97 g).

$^1$H-NMR(DMSO-d$_6$) δ3.59 (3H, s), 3.98 (2H, d, J=5.8 Hz), 7.30 (1H, s), 8.01 (1H, t, J=5.8 Hz), 8.15 (1H, s), 8.39 (1H, s), 9.95 (1H, s)

ESI-MASS: m/z=205(M+H)

Preparation 24

To a solution of benzhydryl 7β-tert-butoxycarbonylamino-3-chloromethyl-3-cephem-4-carboxylate (3.5 g) in N,N-dimethylformamide (4.5 ml) was added sodium iodide (1.02 g), and the mixture was stirred at room temperature for 30 minutes. To the reaction mixture were added 5-formamido-4-formamidomethyl-1-methylpyrazole (3.71 g). The whole mixture was stirred at room temperature for 29 hours and poured into a mixture of ethyl acetate and water. The aqueous layer was separated, and the organic layer was washed with brine, dried over anhydrous magnesium sulfate, and filtered. The filtrate was concentrated to about 20 ml in vacuo. The concentrate was poured into diisopropyl ether (300 ml), and the resulting precipitate was collected by filtration and dried in vacuo. To a solution of the resulting solid in methylene chloride (10.5 ml) were added anisole (3.5 ml) and trifluoroacetic acid (7 ml). The resulting solution was stirred at room temperature for 3 hours and poured into diisopropyl ether. The resulting precipitate was collected by filtration and dried in vacuo to give crude 7β-amino-3-(3-formamido-4-formamidomethyl-2-methyl-1-pyrazolio)methyl-3-cephem-4-carboxylate bistrifluoroacetate (3.07 g). This product was used in the next step without further purification.

EXAMPLE 8

To a solution of crude 7β-amino-3-(3-formamido-4-formamidomethyl-2-methyl-1-pyrazolio)methyl-3-cephem-4-carboxylate bistrifluoroacetate (3.07 g) and N-trimethylsilylacetamide (6.47 g) in a mixed solvent of N,N-dimethylformamide (15 ml) and tetrahydrofuran (15 ml) was added (Z)-2-(5-amino-1,2,4-thiadiazol-3-yl)-2-(1-tert-butoxycarbonyl-1-methylethoxyimino)acetyl chloride hydrochloride salt (1.9 g) under ice-cooling. The solution was stirred under ice-cooling for 2 hours. The reaction mixture was poured into ethyl acetate (300 ml), and the mixture was stirred for 30 minutes. The resulting precipitate was collected by filtration, washed with successively ethyl acetate and diisopropyl ether, and dried in vacuo to give a solid (3.28 g).

To a suspension of the resulting solid in methylene chloride (9 ml) were added anisole (3 ml) and trifluoroacetic acid (6 ml) under ice-cooling. The resulting solution was stirred at room temperature for 3 hours and poured into diisopropyl ether. The resulting precipitate was collected by filtration and dried in vacuo to give crude product of 7β-[(Z)-2-(5-amino-1,2,4-thiadiazol-3-yl)-2-(1-carboxy-1-methylethoxyimino)acetamido]-3-(3-formamido-4-formamidomethyl-2-methyl-1-pyrazolio)methyl-3-cephem-4-carboxylate (3.44 g). This product was used in the next step without further purification.

EXAMPLE 9

To a solution of 7β-[(Z)-2-(5-amino-1,2,4-thiadiazol-3-yl)-2-(1-carboxy-1-methylethoxyimino)acetamido]-3-(3-formamido-4-formamidomethyl-2-methyl-1-pyrazolio)methyl-3-cephem-4-carboxylate (2.5 g) in methanol (25 ml) was added concentrated hydrochloric acid (2.5 ml) at room temperature. The mixture was stirred at room temperature for 17 hours. The reaction mixture was adjusted to about pH 7 with saturated aqueous sodium hydrogencarbonate solution and concentrated in vacuo to remove methanol. The resulting residue was purified by preparative HPLC utilizing ODS column. The eluate containing a desired product was concentrated to about 30 ml in vacuo. The concentrate was adjusted to about pH 1 with concentrated hydrochloric acid and chromatographed on Diaion® HP-20 (Mitsubishi Chemical Corporation) eluting with 20% aqueous 2-propanol. The eluate was concentrated in vacuo and lyophilized to give 7β-[(Z)-2-(5-amino-1,2,4-thiadiazol-3-yl)-2-(1-carboxy-1-methylethoxyimino)acetamido]-3-(3-amino-4-aminomethyl-2-methyl-1-pyrazolio)methyl-3-cephem-4-carboxylate (50 mg) as an amorphous solid.

$^1$H-NMR(D$_2$O) δ1.53 (3H, s), 1.54 (3H, s), 3.20 (1H, d, J=17.8 Hz), 3.48 (1H, d, J=17.8 Hz), 3.73 (3H, s), 4.08 (2H, s), 4.99 (1H, d, J=15.4 Hz), 5.19 (1H, d, J=15.4 Hz), 5.26 (1H, d, J=4.9 Hz), 5.86 (1H, d, J=4.9 Hz), 8.04 (1H, s)

IR(KBr): 3345.9, 3183.9, 1770.3, 1594.8, 1398.1 cm$^{-1}$

ESI-MASS: m/z=595(M+H)

Preparation 25

To a suspension of lithium aluminum hydride (3.01 g) in tetrahydrofuran (150 ml) was added 1-ethyl-5-(tritylamino)-1H-pyrazole-4-carbonitrile (7.5 g) at room temperature. The mixture was refluxed for 55 hours. After cooling on an ice bath, sodium fluoride (13.3 g) and water (6 ml) were added to the reaction mixture. The insoluble materials were removed by filtration. The filtrate was evaporated to give 4-aminomethyl-1-ethyl-5-tritylaminopyrazole (3.4 g).

$^{1}$H-NMR(DMSO-d$_{6}$) δ0.89 (3H, t, J=7.2 Hz), 2.87 (2H, s), 3.18 (2H, q, J=7.2 Hz), 5.71 (1H, s), 6.76 (1H, s), 7.0–7.4 (15H, m)

ESI-MASS: m/z=383(M+H)

Preparation 26

To a solution of 4-aminomethyl-1-ethyl-5-tritylaminopyrazole (3 g) in tetrahydrofuran (30 ml) was added di-tert-butyl dicarbonate (2.05 g). The mixture was stirred at room temperature for 4 hours. The reaction mixture was added to ethyl acetate and water. The aqueous layer was separated, and the organic layer was dried over anhydrous magnesium sulfate and filtered. The filtrate was concentrated in vacuo and purified by column chromatography on silica gel eluting with ethyl acetate/hexane (2:3). The eluate was concentrated in vacuo to give 4-tert-butoxycarbonylaminomethyl-1-ethyl-5-tritylaminopyrazole (2.55 g).

$^{1}$H-NMR(DMSO-d$_{6}$) δ0.88 (3H, t, J=7.2 Hz), 1.36 (9H, s), 3.17 (2H, q, J=7.2 Hz), 3.22 (2H, d, J=5.7 Hz), 5.78 (1H, s), 6.35 (1H, t, J=5.7 Hz), 7.05 (1H, s), 7.1–7.4 (15H, m)

APC-MASS: m/z=482

EXAMPLE 10

To a suspension of a mixture of benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (1 g) and sodium iodide (199 mg) in N,N-dimethylformamide (3 ml) was added 4-tert-butoxycarbonylaminomethyl-1-ethyl-5-tritylaminopyrazole (1.17 g), and the mixture was stirred at room temperature for 47 hours. The reaction mixture was added to a mixture of ethyl acetate (30 ml) and water (20 ml). The organic layer was separated, washed with brine (15 ml), and dried over anhydrous magnesium sulfate. The magnesium sulfate was filtered off, and the filtrate was evaporated to about 5 ml under reduced pressure. The concentrate was poured into diisopropyl ether (150 ml), and the resulting precipitate was collected by filtration and dried in vacuo. To a solution of the resulting solid in methylene chloride (4.5 ml) were added anisole (1.5 ml) and trifluoroacetic acid (3 ml). The resulting solution was stirred at room temperature for 3 hours and poured into diisopropyl ether. The resulting precipitate was collected by filtration and dried in vacuo. The obtained powder was dissolved in a phosphate buffer (pH 7) and adjusted to about pH 6 with saturated aqueous sodium hydrogencarbonate solution. The solution containing the objective compound was purified by preparative HPLC utilizing ODS column. The eluate containing a desired product was concentrated in vacuo. The concentrate was adjusted to about pH 2 with concentrated hydrochloric acid and chromatographed on Diaion® HP-20 (Mitsubishi Chemical Corporation) eluting with 20% aqueous 2-propanol. The eluate was evaporated in vacuo and lyophilized to give 7β-[(Z)-2-(5-amino-1,2,4-thiadiazol-3-yl)-2-(1-carboxy-1-methylethoxyimino)acetamido]-3-(3-amino-4-aminomethyl-2-ethyl-1-pyrazolio)methyl-3-cephem-4-carboxylate (155 mg) as an amorphous solid.

$^{1}$H-NMR(D$_{2}$O) δ1.30 (3H, t, J=7.2 Hz), 1.52 (3H, s), 1.53 (3H, s), 3.17 (1H, d, J=17.8 Hz), 3.48 (1H, d, J=17.8 Hz), 4.06 (2H, s), 4.24 (2H, q, J=7.2 Hz), 5.04 (1H, d, J=15.5 Hz), 5.16 (1H, d, J=15.5 Hz), 5.25 (1H, d, J=4.9 Hz), 5.84 (1H, d, J=4.9 Hz), 8.04 (1H, s)

ESI-MASS: m/z=609(M+H)

Preparation 27

To a solution of 5-amino-1-isopropyl-1H-pyrazole-4-carbonitrile (10.4 g) in pyridine (200 ml) was added triphenylmethyl chloride (23.2 g) at room temperature. The mixture was stirred at 60° C. for 5 hours. The reaction mixture was evaporated under reduced pressure and extracted with ethyl acetate. The extract was dried over anhydrous magnesium sulfate, filtered, and evaporated vacuo. The residue was triturated with diisopropyl ether to give 1-isopropyl-5-tritylamino-1H-pyrazole-4-carbonitrile (19.1 g).

$^{1}$H-NMR(DMSO-d$_{6}$) δ1.18 (6H, d, J=6.5 Hz), 4.61 (1H, qq, J=6.5 Hz), 6.71 (1H, s), 7.1–7.4 (15H, m), 7.51 (1H, s)

ESI-MASS: m/z=415(M+Na)

Preparation 28

To a suspension of lithium aluminum hydride (3.09 g) in tetrahydrofuran (160 ml) was added 1-isopropyl-5-tritylamino-1H-pyrazole-4-carbonitrile (8 g) at room temperature. The mixture was refluxed for 72 hours. After cooling on an ice bath, sodium fluoride (13.7 g) and water (6 ml) were added to the reaction mixture. The insoluble materials were removed by filtration, and the filtrate was evaporated in vacuo. To a solution of the residue in tetrahydrofuran (80 ml) was added di-tert-butyl dicarbonate (6.68 g), and the mixture was stirred at room temperature for 3 hours. The reaction mixture was evaporated in vacuo, and the residue was purified by column chromatography on silica gel eluting with ethyl acetate/hexane (1:3). The eluate was concentrated in vacuo to give 4-tert-butoxycarbonylaminomethyl-1-isopropyl-5-tritylaminopyrazole (3.12 g).

$^{1}$H-NMR(DMSO-d$_{6}$) δ0.80 (6H, d, J=6.6 Hz), 1.36 (9H, s), 3.24 (2H, d, J=5.7 Hz), 4.08 (1H, qq, J=6.6 Hz), 5.73 (1H, s), 6.34 (1H, t, J=5.7 Hz), 7.07 (1H, s), 7.1–7.3 (15H, m)

APC-MASS: m/z=496

EXAMPLE 11

7β-[(Z)-2-(5-Amino-1,2,4-thiadiazol-3-yl)-2-(1-carboxy-1-methylethoxyimino)acetamido]-3-(3-amino-4-aminomethyl-2-isopropyl-1-pyrazolio]methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 4-tert-butoxycarbonylaminomethyl-1-isopropyl-5-tritylaminopyrazole in the same manner as in Example 10.

$^{1}$H-NMR(D$_{2}$O) δ1.4–1.7 (12H, m), 3.10 (1H, d, J=17.6 Hz), 3.44 (1H, d, J=17.6 Hz), 4.07 (2H, s), 4.6–5.0 (1H, m), 5.10 (1H, d, J=15.6 Hz), 5.22 (1H, d, J=15.6 Hz), 5.27 (1H, d, J=4.7 Hz), 5.84 (1H, d, J=4.7 Hz), 8.05 (1H, s)

ESI-MASS: m/z=623(M+H)

Preparation 29

To a suspension of 5-amino-1-propyl-1H-pyrazole-4-carbonitrile (16.32 g) in pyridine (160 ml) was added triphenylmethyl chloride (36.35 g) at room temperature. After stirring at 60° C. for 5 hours, the reaction mixture was evaporated in vacuo. The residue was added to a mixture of tetrahydrofuran and brine, and the organic layer was separated and washed with brine. The extract was dried over anhydrous magnesium sulfate, filtered, and evaporated in vacuo. To the residue was triturated with diisopropyl ether to give 1-propyl-5-tritylamino-1H-pyrazole-4-carbonitrile (37.21 g) as a colorless solid.

$^1$H-NMR(DMSO-$d_6$) δ0.80 (3H, t, J=7.4 Hz), 1.60–1.78 (2H, m), 3.85 (2H, t, J=5.6 Hz), 6.76 (1H, s), 7.22–7.31 (15H, m), 7.48 (1H, s)

Preparation 30

To a suspension of lithium aluminum hydride (8.94 g) in tetrahydrofuran (600 ml) was added 1-propyl-5-tritylamino-1H-pyrazole-4-carbonitrile (37 g) at room temperature. The mixture was refluxed for 7 days. After cooling on an ice bath, sodium fluoride (40 g) and water (17 ml) were added to the reaction mixture. The insoluble materials were removed by filtration. To the filtrate was added ethyl formate, and the mixture was refluxed for 24 hours. After evaporation of the solvent in vacuo, the residue was triturated with diisopropyl ether and dried in vacuo to give 4-aminomethyl-1-propyl-5-tritylaminopyrazole (30.3 g).

$^1$H-NMR(DMSO-$d_6$) δ0.65 (3H, t, J=7.4 Hz), 1.38 (2H, qt, J=7.4 Hz), 2.89 (2H, s), 3.06 (2H, t, J=7.4 Hz), 5.72 (1H, s), 7.1–7.5 (16H, m)

Preparation 31

To a solution of 4-aminomethyl-1-propyl-5-tritylaminopyrazole (9.6 g) in a mixture of ethyl acetate (150 ml) and methanol (30 ml) was added 4N hydrochloric acid in ethyl acetate (24.2 ml), and the mixture was stirred at room temperature for 2 hours. The resulting precipitate was collected by filtration and dried in vacuo to give 4-aminomethyl-1-propyl-5-aminopyrazole dihydrochloride (3.3 g).

$^1$H-NMR(DMSO-$d_6$)δ0.81 (3H, t, J=7.4 Hz), 1.64 (2H, qt, J=7.4 Hz), 3.83 (2H, t, J=7.4 Hz), 3.94 (2H, s), 7.52 (1H, s)

Preparation 32

A solution of 4-aminomethyl-1-propyl-5-aminopyrazole dihydrochloride (3.6 g) in a mixture of tetrahydrofuran (35 ml) and water (35 ml) was adjusted to pH 9 with saturated aqueous sodium carbonate solution, and then to the solution was added a solution of di-tert-butyl dicarbonate (6.92 g) in tetrahydrofuran (15 ml). The mixture was stirred for 1 hour maintaining the pH of the solution at pH 9 with saturated aqueous sodium carbonate solution. The reaction mixture was added to ethyl acetate and water. The aqueous layer was separated, and the organic layer was dried over anhydrous magnesium sulfate and filtered. The filtrate was concentrated in vacuo, and the residue was triturated with diisopropyl ether and dried in vacuo to give 4-tert-butoxycarbonylaminomethyl-1-propyl-5-aminopyrazole (2.21 g).

$^1$H-NMR(DMSO-$d_6$) δ0.82 (3H, t, J=7.4 Hz), 1.37 (9H, s), 1.63 (2H, qt, J=7.4 Hz), 3.75 (2H, t, J=7.4 Hz), 3.76 (2H, d, J=5.8 Hz), 5.02 (2H, s), 6.94 (1H, s), 6.99 (1H, t, J=5.8 Hz)

ESI-MASS: m/z=255(M+H)

Preparation 33
4-tert-Butoxycarbonylaminomethyl-1-propyl-5-tritylaminopyrazole

The title compound was obtained from 4-tert-butoxycarbonylaminomethyl-1-propyl-5-aminopyrazole in the same manner as in Preparation 27.

$^1$H-NMR(DMSO-$d_6$) δ0.64 (3H, t, J=7.4 Hz), 1.3–1.5 (11H, m), 3.05 (2H, t, J=7.4 Hz), 3.23 (2H, d, J=5.7 Hz), 5.79 (1H, s), 6.36 (1H, t, J=5.7 Hz), 7.05 (1H, s), 7.1–7.5 (15H, m)

ESI-MASS: m/z=497(M+H)

EXAMPLE 12

7β-[(Z)-2-(5-Amino-1,2,4-thiadiazol-3-yl)-2-(1-carboxy-1-methylethoxyimino)acetamido]-3-(3-amino-4-aminomethyl-2-propyl-1-pyrazolio]methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 4-tert-butoxycarbonylaminomethyl-1-propyl-5-tritylaminopyrazole in the same manner as in Example 10.

$^1$H-NMR(D$_2$O) δ0.91 (3H, t, J=7.4 Hz), 1.52 (3H, s), 1.53 (3H, s), 1.69 (2H, qt, J=7.4 Hz), 3.15 (1H, d, J=17.8 Hz), 3.45 (1H, d, J=17.8 Hz), 4.07 (2H, s), 4.16 (2H, t, J=7.4 Hz), 5.05 (1H, d, J=15.1 Hz), 5.16 (1H, d, J=15.1 Hz), 5.24 (1H, d, J=4.8 Hz), 5.84 (1H, d, J=4.8 Hz), 8.06 (1H, s)

IR(KBr): 3342.0, 1772.3, 1652.7, 1592.9, 1398.1, 1361.5 cm$^{-1}$

Preparation 34

To a solution of 5-amino-1-(2-hydroxyethyl)-1H-pyrazole-4-carbonitrile (15 g) in methanol (300 ml) was added hydrochloric acid (1.8 ml) under ice-cooling. The resulting solution was stirred for 15 minutes. The mixture was treated with 10% palladium carbon (7.5 g) under a hydrogen atmosphere at room temperature for 3 hours. After the catalyst was filtered off, the filtrate was concentrated in vacuo to give 5-amino-1-(2-hydroxyethyl)-1H-pyrazole-4-carbaldehyde (13.3 g).

$^1$H-NMR(D$_2$O) δ3.82–4.00 (2H, m), 4.06–4.20 (2H, m), 7.99 (1H, s), 9.51 (1H, s)

Preparation 35

To a solution of 5-amino-1-(2-hydroxyethyl)-1H-pyrazole-4-carbaldehyde (40.2 g) in pyridine (400 ml) was added triphenylmethyl chloride (86.7 g) at room temperature. The mixture was stirred at 60° C. for 5 hours. The reaction mixture was evaporated under reduced pressure and extracted with ethyl acetate. The extract was dried over anhydrous magnesium sulfate, filtered, and evaporated in vacuo. The residue was purified by column chromatography on silica gel eluting with ethyl acetate/hexane (3:2) to give 5-amino-1-(2-triphenylmethyloxyethyl)-1H-pyrazole-4-carbaldehyde (62.8 g).

$^1$H-NMR(DMSO-$d_6$) δ3.17 (2H, t, J=4.9 Hz), 4.18 (2H, t, J=4.9 Hz), 6.92 (2H, s), 7.0–7.4 (15H, m), 7.75 (1H, s), 9.57 (1H, s)

ESI-MASS: m/z=420 (M+Na)

Preparation 36

A solution of 5-amino-1-(2-triphenylmethyloxyethyl)-1H-pyrazole-4-carbaldehyde (15 g) and ammonium acetate (4.07 g) in nitromethane (300 ml) was refluxed for 6.5 hours. The reaction mixture was evaporated under reduced pressure and extracted with dichloromethane. The extract was dried over anhydrous magnesium sulfate, filtered, and evaporated in vacuo to give 5-amino-4—[(E)-2-nitroethenyl]-1-(2-triphenylmethyloxyethyl)-1H-pyrazole (4.46 g). $^1$H-NMR (DMSO-$d_6$) δ3.15 (2H, t, J=4.9 Hz), 4.16 (2H, t, J=4.9 Hz), 6.96 (2H, s), 7.1–7.3 (15H, m), 7.75 (1H, d, J=12.9 Hz), 7.83 (1H, s), 8.27 (1H, d, J=12.9 Hz)

IR(KBr): 3421.1, 1660.4, 1600.6, 1546.6, 1319.1, 1294.0, 1265.1, 1216.9, 746.3, 703.9 cm$^{-1}$

ESI-MASS: m/z=463(M+Na)

Preparation 37

To a suspension of lithium aluminum hydride (3.22 g) in tetrahydrofuran (100 ml) was added 5-amino-4-[(E)-2-nitroethenyl]-1-(2-triphenylmethyloxyethyl)-1H-pyrazole (4.4 g) under ice-cooling. The mixture was refluxed for 5 hours. After cooling on an ice bath, sodium fluoride (14.3 g) and water (6.12 ml) were added to the reaction mixture. The insoluble materials were removed by filtration. The filtrate was concentrated in vacuo to give 5-amino-4-(2-aminoethyl)-1-(2-triphenylmethyloxyethyl)-1H-pyrazole (3.63 g). This product was used in the next step without further purification.

Preparation 38

To a solution of 5-amino-4-(2-aminoethyl)-1-(2-triphenylmethyloxyethyl)-1H-pyrazole (3.6 g) in tetrahydrofuran (36 ml) was added di-tert-butyl dicarbonate (2.02 g). The mixture was stirred at room temperature for 19 hours and evaporated in vacuo. The residue was purified by column chromatography on silica gel eluting with ethyl acetate/hexane (2:3). The eluate was concentrated in vacuo to give 5-amino-4-(2-tert-butoxycarbonylaminoethyl)-1-(2-triphenylmethyloxyethyl)-1H-pyrazole (1.79 g).

$^1$H-NMR(DMSO-$d_6$) δ1.36 (9H, s), 2.38 (2H, t, J=7.1 Hz), 3.02 (2H, td, J=7.1 Hz), 3.13 (2H, t, J=5.4 Hz), 4.09 (2H, t, J=5.4 Hz), 4.94 (2H, s), 6.74 (1H, t, J=7.1 Hz), 7.00 (1H, s), 7.2–7.4 (15H, m)

ESI-MASS: m/z=535(M+Na)

EXAMPLE 13

To a solution of 5-amino-4-(2-tert-butoxycarbonylaminoethyl)-1-(2-triphenylmethyloxyethyl)-1H-pyrazole (1.24 g) in dichloromethane (5 ml) were added trimethylsilyl iodide (0.688 ml) and diisopropylethylamine (0.842 ml) under ice-cooling, and the mixture was stirred under ice-cooling for 2 hours. To the reaction mixture was added a mixture of benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (1 g) and sodium iodide (182 mg) in N,N-dimethylformamide (2 ml) which had been stirred under ice-cooling for 30 minutes and at room temperature for 18 hours. The reaction mixture was added to a mixture of ethyl acetate and water. The organic layer was separated and dried over magnesium sulfate. The magnesium sulfate was filtered off, and the filtrate was evaporated to about 20 ml under reduced pressure. The concentrate was poured into diisopropyl ether (150 ml), and the resulting precipitate was collected by filtration and dried in vacuo. To a solution of the resulting solid in methylene chloride (3 ml) were added anisole (1 ml) and trifluoroacetic acid (2 ml). The resulting solution was stirred at room temperature for 3 hours and poured into diisopropyl ether. The resulting precipitate was collected by filtration and dried in vacuo. The obtained powder was dissolved in a phosphate buffer (pH 7) and adjusted to about pH 6 with saturated aqueous sodium hydrogencarbonate solution. The solution containing the objective compound was purified by preparative HPLC utilizing ODS column. The eluate containing a desired product was concentrated in vacuo. The concentrate was adjusted to about pH 2 with concentrated hydrochloric acid and chromatographed on Diaion® HP-20 (Mitsubishi Chemical Corporation) eluting with 20% aqueous 2-propanol. The eluate was evaporated in vacuo and lyophilized to give 7β-[(Z)-2-(5-amino-1,2,4-thiadiazol-3-yl)-2-(1-carboxy-1-methylethoxyimino)acetamido]-3-[3-amino-4-(2-aminoethyl)-2-(2-hydroxyethyl)-1-pyrazolio]methyl-3-cephem-4-carboxylate (66.4 mg) as an amorphous solid.

$^1$H-NMR($D_2O$) δ1.53 (6H, s), 2.82 (2H, t, J=7.4 Hz), 3.15 (1H, d, J=17.5 Hz), 3.22 (2H, t, J=7.4 Hz), 3.49 (1H, d, J=17.5 Hz), 3.87 (2H, t, J=4.7 Hz), 4.37 (2H, t, J=4.7 Hz), 4.99 (1H, d, J=15.2 Hz), 5.10 (1H, d, J=15.2 Hz), 5.26 (1H, d, J=4.8 Hz), 5.84 (1H, d, J=4.8 Hz), 7.88 (1H, s)

IR(KBr): 3336.2, 1770.3, 1648.8, 1596.8, 1400.1 cm$^{-1}$

ESI-MASS: m/z=637(M–H)

Preparation 39

To a suspension of sodium hydride (60% dispersion in mineral oil, 3.46 g) in tetrahydrofuran (250 ml) was added dropwise diethyl(cyanomethyl)phosphonate (23.3 ml) under ice-cooling. The mixture was stirred under ice-cooling for 1 hour. To the reaction mixture was added a solution of 1-(2-triphenylmethyloxyethyl)-5-aminopyrazole-4-carbaldehyde (47.76 g) in tetrahydrofuran (250 ml) at room temperature. The mixture was stirred at room temperature for 5 hours and extracted with ethyl acetate. The extract was washed with aqueous sodium hydrogencarbonate solution, water and brine. The extract was dried over anhydrous magnesium sulfate, filtered, and concentrated in vacuo. The residue was triturated with diisopropyl ether and dried in vacuo to give 4-[(E)-2-cyanoethenyl]-1-[2-(trityloxy)ethyl]-5-aminopyrazole (59.38 g). $^1$H-NMR(DMSO-$d_6$) δ3.13 (2H, t, J=4.9 Hz), 4.15 (2H, t, J=4.9 Hz), 5.59 (1H, d, J=16.3 Hz), 6.35 (2H, s), 7.0–7.4 (15H, m), 7.47 (1H, d, J=16.3 Hz), 7.63 (1H, s)

ESI-MASS: m/z=443(M+Na)

Preparation 40

To a suspension of lithium aluminum hydride (5.41 g) in tetrahydrofuran (200 ml) was added a solution of 4-[(E)-2-cyanoethenyl]-1-[2-(trityloxy)ethyl]-5-aminopyrazole (15 g) in tetrahydrofuran (100 ml) under ice-cooling. The mixture was refluxed for 3.5 hours. After cooling on an ice bath, sodium fluoride (24 g) and water (10.3 ml) were added to the reaction mixture. The insoluble materials were removed by filtration. The filtrate was concentrated in vacuo to give 4-(3-aminopropyl)-1-(2-triphenylmethyloxyethyl)-5-aminopyrazole (13.7 g). This product was used in the next step without further purification.

Preparation 41

To a solution of 4-(3-aminopropyl)-1-(2-triphenylmethyloxyethyl)-5-aminopyrazole (13.7 g) in tetrahydrofuran (140 ml) was added di-tert-butyl dicarbonate (7.72 g). The mixture was stirred at room temperature for 18 hours and evaporated in vacuo. The residue was purified by column chromatography on silica gel eluting with ethyl acetate/hexane (2:3). The eluate was concentrated in vacuo to give 4-(3-tert-butoxycarbonylaminopropyl)-1-(2-triphenylmethyloxyethyl)-5-tert-butoxycarbonylaminopyrazole (2.45 g).

$^1$H-NMR(DMSO-$d_6$) δ1.37 (18H, s), 1.56 (2H, tt, J=6.9 Hz), 2.22 (2H, t, J=6.9 Hz), 2.89 (2H, td, J=6.9 Hz), 3.22 (2H, t, J=6.3 Hz), 4.05 (2H, t, J=6.3 Hz), 6.79 (1H, t, J=6.9 Hz), 7.1–7.4 (16H, m), 8.75 (1H, s)

ESI-MASS: m/z=649(M+Na)

EXAMPLE 14

To a suspension of a mixture benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (1 g) and sodium iodide (182 mg) in N,N-dimethylformamide (2 ml) was added 4-(3-tert-butoxycarbonylaminopropyl)-1-(2-triphenylmethyloxyethyl)-5-tert-butoxycarbonylaminopyrazole (1.52 g), and the mixture was stirred at room temperature for 24 hours. The reaction mixture was added to a mixture of ethyl acetate and water. The organic layer was separated and dried over magnesium sulfate. The magnesium sulfate was filtered off, and the filtrate was evaporated to about 20 ml under reduced pressure. The concentrate was poured into diisopropyl ether (150 ml), and the resulting precipitate was collected by filtration and dried in vacuo. To a solution of the resulting solid in methylene chloride (3 ml) were added anisole (1 ml) and trifluoroacetic acid (2 ml). The resulting solution was stirred at room temperature for 3 hours and poured into diisopropyl ether. The resulting precipitate was collected by filtration and dried in vacuo. The obtained powder was dissolved in a phosphate buffer (pH 7) and adjusted to about pH 6 with saturated aqueous sodium hydrogencarbonate solution. The solution containing the objective compound was purified by preparative HPLC utilizing ODS column. The eluate containing a desired product was concentrated in vacuo. The concentrate was adjusted to about pH 2 with concentrated hydrochloric acid and chromatographed on Diaion® HP-20 (Mitsubishi Chemical Corporation) eluting with 20% aqueous 2-propanol. The eluate was evaporated in vacuo and lyophilized to give 7β-[(Z)-2-(5-amino-1,2,4-thiadiazol-3-yl)-2-(1-carboxy-1-methylethoxyimino)acetamido]-3-[3-amino-4-(3-aminopropyl)-2-(2-hydroxyethyl)-1-pyrazolio]methyl-3-cephem-4-carboxylate (61 mg) as an amorphous solid.

$^1$H-NMR(D$_2$O) δ1.53 (6H, s), 1.94 (2H, quint., J=7.8 Hz), 2.50 (2H, t, J=7.8 Hz), 3.03 (2H, t, J=7.8 Hz), 3.10 (1H, d, J=17.7 Hz), 3.42 (1H, d, J=17.7 Hz), 3.86 (2H, t, J=4.8 Hz), 4.34 (2H, t, J=4.8 Hz), 4.96 (1H, d, J=14.4 Hz), 5.10 (1H, d, J=14.4 Hz), 5.25 (1H, d, J=4.8 Hz), 5.84 (1H, d, J=4.8 Hz), 7.83 (1H, s)

IR(KBr): 3349.7, 1770.3, 1648.8, 1596.8, 1402.0, 1157.1 cm$^{-1}$

ESI-MASS: m/z=653(M+H)

Preparation 42

To a solution of 5-aminopyrazole-4-carbonitrile (102 g) and triethylamine (316 ml) in 1,4-dioxane (2000 ml) was added 1,3-dibromopropane (115 ml), and the mixture was stirred at 95° C. for 5 days. The insoluble materials were removed by filtration, and the filtrate was concentrated in vacuo. To the residue was added 10% aqueous citric acid solution, and the mixture was extracted with chloroform. The extract was dried over anhydrous magnesium sulfate, filtered, and concentrated in vacuo. The residue was triturated with 2-propanol and dried in vacuo to give 4,5,6,7-tetrahydropyrazolo[1,5-a]pyrimidine-3-carbonitrile (8.0 g) as a solid.

$^1$H-NMR(DMSO-$d_6$) δ1.96–2.00 (2H, m), 3.21–3.23 (2H, m), 3.97 (2H, t, J=6.0 Hz), 7.35 (1H, br), 7.54 (1H, s)

Preparation 43

To a solution of 4,5,6,7-tetrahydropyrazolo[1,5-a]pyrimidine-3-carbonitrile (6.9 g) in pyridine (70 ml) was added triphenylmethyl chloride (15.6 g), and the mixture was stirred at 65° C. for 4 hours. After evaporation of the solvent in vacuo, the residue was dissolved in chloroform, and the solution was washed with 10% aqueous citric acid solution. The organic layer was separated, and the aqueous layer was extracted with chloroform. The organic layers were combined, dried over anhydrous magnesium sulfate, filtered, and concentrated in vacuo. The residue was triturated with diisopropyl ether and dried in vacuo to give 4-triphenylmethyl-4,5,6,7-tetrahydropyrazolo[1,5-a]pyrimidine-3-carbonitrile (16.2 g) as a solid.

$^1$H-NMR(CDCl$_3$) δ2.15–2.19 (2H, m), 3.40–3.43 (2H, m), 4.09 (2H, t, J=6.0 Hz), 7.16–7.46 (16H, m)

Preparation 44

To a suspension of lithium aluminum hydride (2.7 g) in tetrahydrofuran (150 ml) was added 4-triphenylmethyl-4,5,6,7-tetrahydropyrazolo[1,5-a]pyrimidine-3-carbonitrile (8.5 g) under ice-cooling. The mixture was stirred at 65° C. for 16 hours. After cooling on an ice bath, potassium fluoride (16.5 g) and water (5 ml) were added to the reaction mixture. The insoluble materials were removed by filtration. The filtrate was concentrated in vacuo to give 1-(4-triphenylmethyl-4,5,6,7-tetrahydropyrazolo[1,5-a]pyrimidin-3-yl)methylamine (8.4 g) as a solid.

$^1$H-NMR(CDCl$_3$) δ2.19–2.24 (2H, m), 3.39 (2H, t, J=5.5 Hz), 3.74 (2H, s), 4.17 (2H, t, J=6.0 Hz), 7.22 (1H, s), 7.34–7.42 (15H, m)

Preparation 45

A suspension of 1-(4-triphenylmethyl-4,5,6,7-tetrahydropyrazolo[1,5-a]pyrimidin-3-yl)methylamine (8.4 g) in ethyl formate (30 ml) was stirred at 50° C. for 16 hours. After evaporation of the solvent in vacuo, the residue was triturated with ethyl acetate and dried in vacuo to give N-[(4,5,6,7-tetrahydropyrazolo[1,5-a]pyrimidin-3-yl)methyl]formamide (3.0 g) as a solid.

$^1$H-NMR(DMSO-$d_6$) δ1.94–1.98 (2H, m), 3.16–3.18 (2H, m), 3.92–3.94 (4H, m), 5.81 (1H, br), 7.00 (1H, s), 7.98 (1H, s), 8.45 (1H, br)

Preparation 46

A solution of silylated N-[(4,5,6,7-tetrahydropyrazolo[1,5-a]pyrimidin-3-yl)methyl]formamide in methylene chloride was prepared by stirring a mixture of N-[(4,5,6,7-tetrahydropyrazolo[1,5-a]pyrimidin-3-yl)methyl]formamide (1.05 g), trimethylsilyl iodide (0.83 ml) and diisopropylethylamine (1.02 ml) in methylene chloride (10 ml) at room temperature for 2.5 hours. To a solution of benzhydryl 7β-tert-butoxycarbonylamino-3-chloromethyl-3-cephem-4-carboxylate (1.0 g) in N,N-dimethylformamide (1 ml) was added sodium iodide (291 mg), and the mixture was stirred at room temperature for 30 minutes. To the resulting solution was added the solution of silylated N-[(4,5,6,7-tetrahydropyrazolo[1,5-a]pyrimidin-3-yl)methyl]formamide prepared above, and the reaction mixture was stirred at room temperature for 3.5 hours. The reaction mixture was poured into a mixture of ethyl acetate and 2 mol/l aqueous potassium hydrogensulfate solution. The aqueous layer was separated, and the organic layer was washed with brine, dried over sodium sulfate and filtered. The filtrate was concentrated to about 20 ml in vacuo. The concentrate was poured into diisopropyl ether (300 ml), and the resulting precipitate was collected by filtration and dried in vacuo. To a suspension of the resulting solid in methylene chloride (3.0 ml) were added anisole (1.0 ml) and trifluoroacetic acid (2.0 ml) under ice-cooling. The resulting solution was stirred at room temperature for 3 hours and poured into diisopropyl ether (300 ml). The resulting precipitate was collected by filtration and dried in vacuo to give crude 7β-amino-3-[3-(formamidomethyl)-4,5,6,7-tetrahydro-1-pyrazolo[1,5-a]pyrimidinio]methyl-3-cephem-4-carboxylate bistrifluoroacetic acid salt (810 mg). This product was used in the next step without further purification.

EXAMPLE 15

To a solution of crude 7δ-amino-3-[3-(formamidomethyl)-4,5,6,7-tetrahydro-1-pyrazolo[1,5-a]pyrimidinio]methyl-3-cephem-4-carboxylate bistrifluoroacetic acid salt (800 mg) in a mixed solvent of N,N-dimethylformamide (16 ml) and tetrahydrofuran (16 ml) was added N-trimethylsilylacetamide (2.94 g) at room temperature. The mixture was stirred at room temperature for 15 minutes. To the reaction mixture was added (Z)-2-(5-amino-1,2,4-thiadiazol-3-yl)-2-(1-tert-butoxycarbonyl-1-methylethoxyimino)acetyl chloride hydrochloride salt (420 mg) under ice-cooling. The mixture was stirred under ice-cooling for 2 hours. The reaction mixture was poured into ethyl acetate (250 ml), and the mixture was stirred for 30 minutes. The resulting precipitate was collected by filtration, washed with successively ethyl acetate and diisopropyl ether, and dried in vacuo to give a solid (610 mg).

To a suspension of the resulting solid in methylene chloride (1.8 ml) were added anisole (0.6 ml) and trifluoroacetic acid (1.2 ml) under ice-cooling. The resulting solution was stirred at room temperature for 3 hours and poured into diisopropyl ether (150 ml). The resulting precipitate was collected by filtration and dried in vacuo to give a crude product, which was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)acetamido)]-3-[3-(formamidomethyl)-4,5,6,7-tetrahydro-1-pyrazolo[1,5-a]pyrimidinio]methyl-3-cephem-4-carboxylate (130 mg) as an amorphous solid.

$^1$H-NMR(D$_2$O) δ1.60 (3H, s), 1.60 (3H, s), 2.05–2.25 (2H, m), 3.18 and 3.35 (2H, ABq, J=17.5 Hz), 3.3–3.5 (2H, m), 4.0–4.25 (2H, m), 4.19 (2H, s), 4.91 and 5.21 (2H, ABq, J=16.0 Hz), 5.23 (1H, d, J=4.5 Hz), 5.87 (1H, d, J=4.5 Hz), 7.83 (1H, s), 8.11 (1H, s)

EXAMPLE 16

A solution of 7β-[(Z)-2-(5-amino-1,2,4-thiadiazol-3-yl)-2-(1-carboxy-1-methylethoxyimino)acetamido]-3-[3-(formamidomethyl)-4,5,6,7-tetrahydro-1-pyrazolo[1,5-a]pyrimidinio]methyl-3-cephem-4-carboxylate (130 mg) in 10% aqueous hydrochloric acid (4.36 ml) was stirred at room temperature for 6 hours. The reaction mixture was purified by preparative HPLC utilizing ODS column. The eluate containing a desired product was concentrated to about 30 ml in vacuo. The concentrate was adjusted to about pH 3 with concentrated hydrochloric acid and chromatographed on Diaion® HP-20 (Mitsubishi Chemical Corporation) eluting with 30% aqueous 2-propanol. The eluate was concentrated to about 30 ml in vacuo and lyophilized to give 7β-[(Z)-2-(5-amino-1,2,4-thiadiazol-3-yl)-2-(1-carboxy-1-methylethoxyimino)acetamido]-3-(3-aminomethyl-4,5,6,7-tetrahydro-1-pyrazolo[1,5-a]pyrimidinio)methyl-3-cephem-4-carboxylate (48 mg) as an amorphous solid.

$^1$H-NMR(D$_2$O) δ1.54 (3H, s), 1.55 (3H, s), 2.05–2.3 (2H, m), 3.23 and 3.48 (2H, ABq, J=17.8 Hz), 3.35–3.5 (2H, m), 4.03 (2H, s), 4.1–4.2 (2H, m), 4.88 and 5.19 (2H, ABq, J=15.5 Hz), 5.25 (1H, d, J=4.8 Hz), 5.87 (1H, d, J=4.8 Hz), 7.98 (1H, s)

Preparation 47

To N,N-dimethylformamide (307 ml) was added dropwise phosphorus oxychloride (123 ml) under ice-cooling. To the mixture was added a solution of 4,5,6,7-tetrahydropyrazolo[1,5-a]pyrimidine-4-carbaldehyde (100 g) in N,N-dimethylformamide (200 ml) under ice-cooling. The reaction mixture was stirred at 80° C. for 2 hours. After cooling, water was added to the reaction mixture, and the mixture was neutralized with sodium carbonate. The mixture was extracted with chloroform. The organic layer was dried over anhydrous magnesium sulfate, filtered, and concentrated in vacuo. The residue was triturated with hexane and dried in vacuo to give 4,5,6,7-tetrahydropyrazolo[1,5-a]pyrimidine-3-carbaldehyde (65 g) as a solid.

$^1$H-NMR(CDCl$_3$) δ2.16–2.21 (2H, m), 3.43–3.45 (2H, m), 4.07–4.09 (2H, m), 6.30 (1H, br), 7.57 (1H, s), 9.56 (1H, s)

Preparation 48

To a suspension of sodium hydride (60% dispersion in mineral oil, 14.4 g) in tetrahydrofuran (300 ml) was added dropwise triethyl phosphonoacetate (81.0 g) under ice-cooling. The mixture was stirred under ice-cooling for 1 hour. To the reaction mixture was added 4,5,6,7-tetrahydropyrazolo[1,5-a]pyrimidine-3-carbaldehyde (45.5 g), and the mixture was stirred at room temperature for 17 hours. After evaporation of the solvent in vacuo, the residue was dissolved in chloroform, and the solution was washed with water. The organic layer was dried over anhydrous magnesium sulfate, filtered, and concentrated in vacuo. The residue was triturated with diethyl ether and dried in vacuo to give ethyl 3-(4,5,6,7-tetrahydropyrazolo[1,5-a]pyrimidin-3-yl)acrylate (49.2 g) as a solid.

$^1$H-NMR(CDCl$_3$) δ1.30 (3H, t, J=7.3 Hz), 2.15–2.19 (2H, m), 3.41–3.43 (2H, m), 4.08–4.12 (2H, m), 4.21 (2H, q, J=7.3 Hz), 4.47 (1H, br), 5.78 (1H, d, J=16.0 Hz), 7.44 (1H, s), 7.47 (1H, d, J=16.0 Hz)

Preparation 49

A solution of ethyl 3-(4,5,6,7-tetrahydropyrazolo[1,5-a]pyrimidin-3-yl)acrylate (45 g) in a mixture of ethanol (800 ml) and tetrahydrofuran (400 ml) was treated with 10% palladium carbon (2.2 g) under a hydrogen atmosphere at room temperature for 22 hours. After the catalyst was filtered off, the filtrate was concentrated in vacuo to give ethyl 3-(4,5,6,7-tetrahydropyrazolo[1,5-a]pyrimidin-3-yl) propionate (50 g) as an oil.

$^1$H-NMR(CDCl$_3$) δ1.23 (3H, t, J=7.0 Hz), 2.08–2.13 (2H, m), 2.49–2.57 (4H, m), 3.28–3.31 (2H, m), 4.07–4.12 (4H, m), 4.45 (1H, br), 7.11 (1H, s)

Preparation 50

A mixture of ethyl 3-(4,5,6,7-tetrahydropyrazolo[1,5-a]pyrimidin-3-yl)propionate (20 g) and 1 mol/l aqueous sodium hydroxide solution (100 ml) was stirred at room temperature for 16 hours. The reaction mixture was neutralized with concentrated hydrochloric acid, and the mixture was concentrated in vacuo. The residue was dissolved in methanol, and the insoluble sodium chloride was removed by filtration. The filtrate was concentrated in vacuo to give crude 3-(4,5,6,7-tetrahydropyrazolo[1,5-a]pyrimidin-3-yl)propionic acid as an oil. This product was used in the next step without further purification.

To formic acid (50 ml) was added acetic anhydride (60 ml), and the mixture was stirred at 40° C. for 2 hours. The resulting mixture was added to the above oily product [3-(4,5,6,7-tetrahydropyrazolo[1,5-a]pyrimidin-3-yl)propionic acid] and the mixture was stirred at room temperature for 15 hours. After evaporation of the solvent in vacuo, to the residue was added water. The mixture was neutralized with saturated aqueous sodium hydrogencarbonate solution, and concentrated in vacuo. The residue was dissolved in methanol, and the insoluble materials were removed by filtration. The filtrate was concentrated in vacuo to give 3-(4-formyl-4,5,6,7-tetrahydropyrazolo[1,5-a]pyrimidin-3-yl)propionic acid (23 g) as an oil.

$^1$H-NMR(CDCl$_3$) δ2.02–2.07 (2H, m), 2.49–2.52 (2H, m), 2.62–2.67 (2H, m), 3.75–3.78 (2H, m), 4.08–4.12 (2H, m), 7.30 (1H, s), 8.61 (1H, s)

Preparation 51

To a mixture of 3-(4-formyl-4,5,6,7-tetrahydropyrazolo[1,5-a]pyrimidin-3-yl)propionic acid (18.0 g), triethylamine (9.8 g) and tetrahyrofuran (300 ml) was added dropwise ethyl chloroformate (9.6 g) under ice-cooling. The mixture was stirred under ice-cooling for 30 minutes. To the reaction mixture was added a solution of sodium azide (6.68 g) in water (100 ml), and the mixture was stirred at room temperature for 30 minutes. To the reaction mixture was added methylene chloride, and the aqueous layer was separated. The organic layer was washed with water, dried over anhydrous magnesium sulfate, filtered, and concentrated in vacuo. To the oily residue was added methanol (100 ml), and the mixture was stirred under reflux for 1.5 hours. The reaction mixture was concentrated in vacuo to give crude methyl N-[2-(4-formyl-4,5,6,7-tetrahydropyrazolo[1,5-a]pyrimidin-3-yl)ethyl]carbamate as an oil. This product was used in the next step without further purification.

A mixture of the crude product [methyl N-[2-(4-formyl-4,5,6,7-tetrahydropyrazolo[1,5-a]pyrimidin-3-yl)ethyl]carbamate] and concentrated hydrochloric acid (60 ml) was stirred under reflux for 16 hours. To the reaction mixture was added water, and the mixture was adjusted to pH 5 with aqueous sodium hydroxide solution. The solution was washed with methylene chloride, and the aqueous layer was adjusted to pH 8 with saturated aqueous sodium hydrogencarbonate solution. To the solution was added di-tert-butyl dicarbonate (10.0 g), and the mixture was stirred at room temperature for 1 hour. The reaction mixture was extracted with methylene chloride. The organic layer was dried over anhydrous magnesium sulfate, filtered, and concentrated in vacuo. To the oily residue were added methanol (50 ml) and 4 mol/l hydrogen chloride solution in dioxane (50 ml), and the mixture was stirred under reflux for 30 minutes. After evaporation of the solvent in vacuo, the residue was triturated with 2-propanol and dried in vacuo to give 2-(4,5,6,7-tetrahydropyrazolo[1,5-a]pyrimidin-3-yl)ethylamine dihydrochloride (5.5 g) as a solid.

$^1$H-NMR(DMSO-d$_6$) δ2.03–2.05 (2H, m), 2.70–2.73 (2H, m), 2.93–2.97 (2H, m), 3.27–3.30 (2H, m), 4.11–4.14 (2H, m), 7.89 (1H, s)

Preparation 52

To a solution of 2-(4,5,6,7-tetrahydropyrazolo[1,5-a]pyrimidin-3-yl)ethylamine dihydrochloride (2.36 g) and ethyl formate (40 g) in methanol (20 ml) was added 28% sodium methoxide solution in methanol (4.0 g), and the mixture was stirred under reflux for 16 hours. The insoluble materials were filtered off using Celite, and the filtrate was concentrated in vacuo. The residue was triturated with acetonitrile and dried in vacuo to give N-[2-(4,5,6,7-tetrahydropyrazolo[1,5-a]pyrimidin-3-yl)ethyl]formamide (1.2 g) as a solid.

$^1$H-NMR(DMSO-d$_6$) δ1.92–1.97 (2H, m), 2.32–2.50 (2H, m), 3.10–3.17 (4H, m), 3.91–3.93 (2H, m), 5.69 (1H, br), 6.95 (1H, s), 7.98 (1H, s)

Preparation 53

7β-Amino-3-[3-(2-formamidoethyl)-(4,5,6,7-tetrahydro-1-pyrazolo[1,5-a]pyrimidinio]methyl-3-cephem-4-carboxylate bistrifluoroacetic acid salt The title compound was obtained from benzhydryl 7β-tert-butoxycarbonylamino-3-chloromethyl-3-cephem-4-carboxylate and N-[2-(4,5,6,7-tetrahydropyrazolo[1,5-a]pyrimidin-3-yl)ethyl]formamide in the same manner as in Preparation 46.

EXAMPLE 17

7β-[(Z)-2-(5-Amino-1,2,4-thiadiazol-3-yl)-2-(1-carboxy-1-methylethoxyimino)acetamido]-3-[3-(2-formamidoethyl)-4,5,6,7-tetrahydro-1-pyrazolo[1,5-a]pyrimidinio]methyl-3-cephem-4-carboxylate The title compound was obtained from 7β-amino-3-[3-(2-formamidoethyl)-(4,5,6,7-tetrahydro-1-pyrazolo[1,5-a]pyrimidinio]methyl-3-cephem-4-carboxylate bistrifluoroacetic acid salt in the same manner as in Example 15.

$^1$H-NMR(D$_2$O) δ1.56 (3H, s), 1.57 (3H, s), 2.0–2.25 (2H, m), 2.59 (2H, t, J=6.5 Hz), 3.15 and 3.31 (2H, ABq, J=17.8 Hz), 3.3–3.5 (4H, m), 4.0–4.2 (2H, m), 4.88 and 5.18 (2H, ABq, J=16.0 Hz), 5.23 (1H, d, J=4.5 Hz), 5.86 (1H, d, J=4.5 Hz), 7.71 (1H, s), 8.02 (1H, s)

EXAMPLE 18

7β-[(Z)-2-(5-Amino-1,2,4-thiadiazol-3-yl)-2-(1-carboxy-1-methylethoxyimino)acetamido]-3-[3-(2-aminoethyl)-4,5,6,7-tetrahydro-1-pyrazolo[1,5-a]pyrimidinio]methyl-3-cephem-4-carboxylate The title compound was obtained from 7β-[(Z)-2-(5-amino-1,2,4-thiadiazol-3-yl)-2-(1-carboxy-1-methylethoxyimino)acetamido]-3-[3-(2-formamidoethyl)-4,5,6,7-tetrahydro-1-pyrazolo[1,5-a]pyrimidinio]methyl-3-cephem-4-carboxylate in the same manner as in Example 16.

$^1$H-NMR(D$_2$O) δ1.54 (3H, s), 1.55 (3H, s), 2.05–2.25 (2H, m), 2.76 (2H, t, J=7.5 Hz), 3.18 (2H, t, J=7.5 Hz), 3.22 and 3.47 (3H, ABq, J=18.0 Hz), 3.25–3.5 (2H, m), 4.05–4.2 (2H, m), 4.87 and 5.12 (2H, ABq, J=15.5 Hz), 5.25 (1H, d, J=4.8 Hz), 5.85 (1H, d, J=4.8 Hz), 7.76 (1H, s)

Preparation 54

A solution of ethyl 3-(4,5,6,7-tetrahydropyrazolo[1,5-a]pyrimidin-3-yl)propionate (30 g) in saturated methanolic ammonia solution (700 ml) was stirred at 110° C. for 5 days in an autoclave. After evaporation of the solvent in vacuo, methylene chloride was added to the residue. The resulting solid was collected by filtration and dissolved in methanol. To the solution was added activated charcoal, and the mixture was filtered. The filtrate was concentrated in vacuo. The residue was triturated with acetonitrile and dried in vacuo to give 3-(4,5,6,7-tetrahydropyrazolo[1,5-a]pyrimidin-3-yl)propionamide (11.3 g) as a solid.

¹H-NMR(DMSO-d₆) δ1.92–1.96 (2H, m), 2.18–2.21 (2H, m), 2.38–2.41 (2H, m), 3.12–3.14 (2H, m), 3.90–3.92 (2H, m), 5.69 (1H, br), 6.73 (1H, br), 6.91 (1H, s)

Preparation 55

To a suspension of lithium aluminum hydride (7.6 g) in tetrahydrofuran (300 ml) was added 3-(4,5,6,7-tetrahydropyrazolo[1,5-a]pyrimidin-3-yl)propionamide (10 g) at room temperature. The mixture was stirred under reflux for 2 days. After cooling on an ice bath, potassium fluoride (34 g) and water (10 ml) were added to the reaction mixture. The insoluble materials were removed by filtration. To the filtrate were added 10% aqueous sodium carbonate solution (100 ml) and di-tert-butyl dicarbonate (20.0 g). The mixture was stirred at room temperature for 1 hour. After evaporation of the solvent in vacuo, the residue was dissolved in chloroform. The solution was washed with water, dried over anhydrous magnesium sulfate, filtered, and concentrated in vacuo. To the oily residue were added methanol (100 ml) and 4 mol/l hydrogen chloride solution in dioxane (50 ml), and the mixture was stirred under reflux for 30 minutes. The reaction mixture was concentrated in vacuo to give crude 3-(4,5,6,7-tetrahydropyrazolo[1,5-a]pyrimidin-3-yl)propylamine (7.0 g) as an oil. This product was used in the next step without further purification.

To a solution of the crude product [3-(4,5,6,7-tetrahydropyrazolo[1,5-a]pyrimidin-3-yl)propylamine] (7.0 g) in methanol (60 ml) was added 28% sodium methoxide solution in methanol (12 g), followed by the addition of ethyl formate (120 g). The mixture was stirred under reflux for 20 hours. The mixture was filtered through Celite, and the filtrate was concentrated in vacuo. The oily residue was purified by column chromatography on silica gel eluting with chloroform/methanol to give N-[3-(4,5,6,7-tetrahydropyrazolo[1,5-a]pyrimidin-3-yl)propyl]formamide (3.1 g) as an oil.

¹H-NMR(CDCl₃) δ1.70–1.76 (2H, m), 2.10–2.15 (2H, m), 2.29–2.31 (2H, m), 3.29–3.33 (4H, m), 4.09–4.12 (2H, m), 4.20 (1H, br), 5.82 (1H, br), 7.11 (1H, s), 8.17 (1H, s)

Preparation 56

7β-Amino-3-[3-(3-formamidopropyl)-(4,5,6,7-tetrahydro-1-pyrazolo[1,5-a]pyrimidinio]methyl-3-cephem-4-carboxylate bistrifluoroacetic acid salt The title compound was obtained from benzhydryl 7β-tert-butoxycarbonylamino-3-chloromethyl-3-cephem-4-carboxylate and N-[3-(4,5,6,7-tetrahydropyrazolo[1,5-a]pyrimidin-3-yl)propyl]formamide in the same manner as in Preparation 46.

EXAMPLE 19

7β-[(Z)-2-(5-Amino-1,2,4-thiadiazol-3-yl)-2-(1-carboxy-1-methylethoxyimino)acetamido]-3-[3-(3-formamidopropyl)-4,5,6,7-tetrahydro-1-pyrazolo[1,5-a]pyrimidinio]methyl-3-cephem-4-carboxylate The title compound was obtained from 7β-amino-3-[3-(3-formamidopropyl)-(4,5,6,7-tetrahydro-1-pyrazolo[1,5-a]pyrimidinio]methyl-3-cephem-4-carboxylate bistrifluoroacetic acid salt in the same manner as in Example 15.

¹H-NMR(D₂O) δ1.60 (3H, s), 1.61 (3H, s), 1.77 (2H, quintet, J=7.0 Hz), 2.2–2.25 (2H, m), 2.38 (2H, t, J=7.0 Hz), 3.13 and 3.33 (2H, ABq, J=17.5 Hz), 3.23 (2H, t, J=7.0 Hz), 3.25–3.45 (2H, m), 4.0–4.2 (2H, m), 4.87 and 5.19 (2H, ABq, J=16.0 Hz), 5.23 (1H, d, J=5.0 Hz), 5.86 (1H, d, J=5.0 Hz), 7.68 (1H, s), 8.04 (1H, s)

EXAMPLE 20

7β-[(Z)-2-(5-Amino-1,2,4-thiadiazol-3-yl)-2-(1-carboxy-1-methylethoxyimino)acetamido]-3-[3-(3-aminopropyl)-4,5,6,7-tetrahydro-1-pyrazolo[1,5-a]pyrimidinio]methyl-3-cephem-4-carboxylate The title compound was obtained from 7β-[(Z)-2-(5-amino-1,2,4-thiadiazol-3-yl)-2-(1-carboxy-1-methylethoxyimino)acetamido]-3-[3-(3-formamidopropyl)-4,5,6,7-tetrahydro-1-pyrazolo[1,5-a]pyrimidinio]methyl-3-cephem-4-carboxylate in the same manner as in Example 16.

¹H-NMR(D₂O) δ1.53 (3H, s), 1.54 (3H, s), 1.90 (2H, quintet, J=7.5 Hz), 2.0–2.2 (2H, m), 2.42 (2H, t, J=7.5 Hz), 3.01 (2H, t, J=7.5 Hz), 3.19 and 3.38 (2H, ABq, J=18.0 Hz), 3.25–3.45 (2H, m), 4.0–4.2 (2H, m), 4.84 and 5.13 (2H, ABq, J=15.5 Hz), 5.23 (1H, d, J=4.8 Hz), 5.85 (1H, d, J=4.8 Hz), 7.69 (1H, s)

Preparation 57

To phosphoric trichloride (136 ml) was added N,N-dimethylformamide (339 ml) under ice-cooling, and the mixture was stirred under ice-cooling for 30 minutes. To the mixture was added a solution of 2,3-dihydro-1H-imidazo[1,2-b]pyrazole-1-carbaldehyde (100 g) in N,N-dimethylformamide (200 ml), and the mixture was stirred at 80° C. for 1.5 hours. The reaction mixture was carefully added to a mixture of ethyl acetate and water under ice-cooling, and the mixture was adjusted to pH 6. The organic layer was dried over anhydrous magnesium sulfate, filtered, and concentrated in vacuo. The residue was triturated with diisopropyl ether and dried in vacuo to give 2,3-dihydro-1H-imidazo[1,2-b]pyrazole-1,7-dicarbaldehyde (102 g).

¹H-NMR(DMSO-d₆) δ4.39 (4H, m), 7.82 (1H, s), 9.52 (1H, s), 9.67 (1H, s)

IR(KBr): 1672, 1558.2, 1527.3, 844.7 cm⁻¹

Preparation 58

A solution of 2,3-dihydro-1H-imidazo[1,2-b]pyrazole-1,7-dicarbaldehyde (1 g) and ammonium acetate (653 mg) in nitromethane (20 ml) was refluxed for 4 hours. The reaction mixture was evaporated under reduced pressure and extracted with dichloromethane. The extract was dried over anhydrous magnesium sulfate, filtered, and concentrated in vacuo to give 7-[(E)-2-nitroethenyl]-2,3-dihydro-1H-imidazo[1,2-b]pyrazole-1-carbaldehyde (1.00 g).

IR(KBr): 1689.3, 1608.3, 1517.7, 1483.0, 1328.7, 1311.4 cm⁻¹

ESI-MASS: m/z=231(M+Na)

Preparation 59

To a suspension of lithium aluminum hydride (465 mg) in tetrahydrofuran (10 ml) was added 7-[(E)-2-nitroethenyl]-2,3-dihydro-1H-imidazo[1,2-b]pyrazole-1-carbaldehyde (300 mg) under ice-cooling. The mixture was refluxed for 1.5 hours. After cooling on an ice bath, sodium fluoride (2.06 g) and water (0.882 ml) were added to the reaction mixture. The insoluble materials were removed by filtration. The filtrate was concentrated in vacuo to give 2-(2,3-dihydro-1H-imidazo[1,2-b]pyrazol-7-yl)ethylamine (165 mg). This product was used in the next step without further purification.

APC-MASS: m/z=153(M+H)

Preparation 60

A suspension of 2-(2,3-dihydro-1H-imidazo[1,2-b]pyrazol-7-yl)ethylamine (155 mg) in ethyl formate (3 ml) was refluxed for 4.5 hours. After evaporation of the solvent in vacuo, the residue was triturated with ethyl acetate and dried in vacuo to give 2-(2,3-dihydro-1H-imidazo[1,2-b]pyrazol-7-yl)ethylformamide (165 mg) as a solid.

$^1$H-NMR (DMSO-$d_6$) δ2.36 (2H, t, J=7.2 Hz), 3.18 (2H, td, J=7.2 Hz), 3.7–3.9 (2H, m), 3.9–4.1 (2H, m), 5.48 (1H, s), 7.05 (1H, s), 7.9–8.1 (1H, m)

IR(KBr): 1668.1, 1658.5, 1523.5 cm$^{-1}$

APC-MASS: m/z=181 (M+H)

Preparation 61

To a solution of 2-(2,3-dihydro-1H-imidazo[1,2-b]pyrazol-7-yl)ethylformamide (1.67 g) in pyridine (15 ml) was added triphenylmethyl chloride (3.1 g) at room temperature. The mixture was stirred at 60° C. for 5.5 hours. The reaction mixture was evaporated under reduced pressure and extracted with ethyl acetate. The extract was dried over anhydrous magnesium sulfate, filtered, and concentrated in vacuo. The residue was purified by column chromatography on silica gel eluting with ethyl acetate to give 2-(1-trityl-2,3-dihydro-1H-imidazo[1,2-b]pyrazol-7-yl)ethylformamide (610 mg).

EXAMPLE 21

To a suspension of a mixture of benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (0.5 g) and sodium iodide (99.6 mg) in N,N-dimethylformamide (1 ml) was added 2-(1-trityl-2,3-dihydro-1H-imidazo[1,2-b]pyrazol-7-yl)ethylformamide (587 mg), and the mixture was stirred at room temperature for 24 hours. The reaction mixture was added to a mixture of ethyl acetate and water. The organic layer was separated and dried over magnesium sulfate. The magnesium sulfate was filtered off, and the filtrate was evaporated to about 20 ml under reduced pressure. The concentrate was poured into diisopropyl ether (80 ml), and the resulting precipitate was collected by filtration and dried in vacuo. To a solution of the resulting solid in methylene chloride (3 ml) were added anisole (1 ml) and trifluoroacetic acid (2 ml). The resulting solution was stirred at room temperature for 3 hours and poured into diisopropyl ether. The resulting precipitate was collected by filtration and dried in vacuo. The obtained powder was dissolved in a phosphate buffer (pH 7) and adjusted to about pH 6 with saturated aqueous sodium hydrogencarbonate solution. The solution containing the objective compound was purified by preparative HPLC utilizing ODS column. The eluate containing a desired product was concentrated in vacuo. The concentrate was adjusted to about pH 2 with concentrated hydrochloric acid and chromatographed on Diaion® HP-20 (Mitsubishi Chemical Corporation) eluting with 20% aqueous 2-propanol. The eluate was evaporated in vacuo and lyophilized to give 7β-[(Z)-2-(5-amino-1,2,4-thiadiazol-3-yl)-2-(1-carboxy-1-methylethoxyimino)acetamido]-3-[2,3-dihydro-7-(2-formamidoethyl)-5-(1H-imidazo[1,2-b]pyrazolio)]methyl-3-cephem-4-carboxylate (154 mg) as an amorphous solid.

$^1$H-NMR(D$_2$O) δ1.58 (6H, s), 2.59 (2H, t, J=6.5 Hz), 3.21 (1H, d, J=17.7 Hz), 3.40 (2H, t, J=6.5 Hz), 3.44 (1H, d, J=17.7 Hz), 4.0–4.4 (4H, m), 4.88 (1H, d, J=15.4 Hz), 5.06 (1H, d, J=15.4 Hz), 5.24 (1H, d, J=4.8 Hz), 5.85 (1H, d, J=4.8 Hz), 7.86 (1H, s), 8.01 (1H, s)

IR(KBr): 3392.2, 3280.3, 1772.3, 1670.1, 1612.2 cm$^{-1}$

ESI-MASS: m/z=647(M−1)

EXAMPLE 22

To a solution of 7β-[(Z)-2-(5-amino-1,2,4-thiadiazol-3-yl)-2-(1-carboxy-1-methylethoxyimino)acetamido]-3-[2,3-dihydro-7-(2-formamidoethyl)-5-(1H-imidazo[1,2-b]pyrazolio)]methyl-3-cephem-4-carboxylate (147 mg) in methanol (1.5 ml) was added concentrated hydrochloric acid (0.15 ml) at room temperature. The mixture was stirred at room temperature for 4 hours and poured into ethyl acetate. The resulting precipitate was collected by filtration and dried in vacuo. The obtained powder was dissolved in a phosphate buffer (pH 7) and adjusted to about pH 6 with saturated aqueous sodium hydrogencarbonate solution. The solution containing the objective compound was purified by preparative HPLC utilizing ODS column. The eluate containing a desired product was concentrated in vacuo. The concentrate was adjusted to about pH 2 with concentrated hydrochloric acid and chromatographed on Diaion® HP-20 (Mitsubishi Chemical Corporation) eluting with 20% aqueous 2-propanol. The eluate was evaporated in vacuo and lyophilized to give 7β-[(Z)-2-(5-amino-1,2,4-thiadiazol-3-yl)-2-(1-carboxy-1-methylethoxyimino)acetamido]-3-[2,3-dihydro-7-(2-aminoethyl)-5-(1H-imidazo[1,2-b]pyrazolio)]methyl-3-cephem-4-carboxylate (32.4 mg).

$^1$H-NMR(D$_2$O) δ1.53 (3H, s), 1.54 (3H, s), 2.79 (2H, t, J=7.4 Hz), 3.19 (2H, t, J=7.4 Hz), 3.28 (1H, d, J=17.7 Hz), 3.56 (1H, d, J=17.7 Hz), 4.0–4.5 (4H, m), 4.9–5.1 (2H, m), 5.26 (1H, d, J=4.8 Hz), 5.85 (1H, d, J=4.8 Hz), 7.93 (1H, s)

ESI-MASS: m/z=619(M−H)

Preparation 62

To a suspension of sodium hydride (60% dispersion in mineral oil, 16 g) in tetrahydrofuran (600 ml) was added dropwise triethyl phohphonoacetate (80 ml) under ice-cooling. The mixture was stirred under ice-cooling for 1 hour. To the reaction mixture was added 2,3-dihydro-1H-imidazo[1,2-b]pyrazole-1,7-dicarbaldehyde (60 g) at room temperature, and the mixture was stirred at room temperature for 2.5 hours. To the reaction mixture was added saturated aqueous ammonium chloride solution and extracted with ethyl acetate. The extract was dried over anhydrous magnesium sulfate, filtered, and concentrated in vacuo. The residue was triturated with diisopropyl ether and dried in vacuo to give ethyl (2E)-3-(1-formyl-2,3-dihydro-1H-imidazo[1,2-b]pyrazol-7-yl)-2-propenoate (63.5 g). This product was used in the next step without further purification.

Preparation 63

A solution of ethyl (2E)-3-(1-formyl-2,3-dihydro-1H-imidazo[1,2-b]pyrazol-7-yl)-2-propenoate (40 g) in a mixture of ethanol (200 ml) and tetrahydrofuran (500 ml) was treated with 10% palladium carbon (10 g) under a hydrogen atmosphere at room temperature for 4.5 hours. After the catalyst was filtered off, the filtrate was concentrated in vacuo to give ethyl 3-(1-formyl-2,3-dihydro-1H-imidazo[1,2-b]pyrazol-7-yl)propanoate (40.1 g). This product was used in the next step without further purification.

Preparation 64

A solution of ethyl 3-(1-formyl-2,3-dihydro-1H-imidazo[1,2-b]pyrazol-7-yl)propanoate (10 g) in a mixture of methanol (50 ml) and an aqueous solution of 28% ammonia (104 ml) was stirred at room temperature for 41 hours. After evaporation of the solvent in vacuo, the residue was triturated with diisopropyl alcohol, dried in vacuo to give 3-(2,3-dihydro-1H-imidazo[1,2-b]pyrazol-7-yl)propanamide (6.44 g).

¹H-NMR(DMSO-d₆) δ2.1–2.5 (4H, m), 3.5–4.0 (4H, m), 6.72 (1H, s), 7.00 (1H, s), 7.25 (1H, s), 8.42 (1H, s)

APC-MASS: m/z=181(M+H)

Preparation 65

To a solution of 3-(2,3-dihydro-1H-imidazo[1,2-b]pyrazol-7-yl)propanamide (6 g) in pyridine (60 ml) was added triphenylmethyl chloride (11.1 g) at room temperature. The mixture was stirred at 60° C. for 17 hours. The reaction mixture was evaporated under reduced pressure and extracted with ethyl acetate. The extract was dried over anhydrous magnesium sulfate, filtered, and evaporated in vacuo. The residue was triturated with diisopropyl ether and dried in vacuo to give 3-(1-trityl-2,3-dihydro-1H-imidazo[1,2-b]pyrazol-7-yl)propanamide (11.2 g).

¹H-NMR(DMSO-d₆) δ1.40 (2H, t, J=7.1 Hz), 1.83 (2H, t, J=7.1 Hz), 3.44 (2H, t, J=7.5 Hz), 3.80 (2H, t, J=7.5 Hz), 6.58 (1H, s), 6.97 (1H, s), 7.01 (1H, s), 7.1–7.5 (15H, m)

ESI-MASS: m/z=445(M+Na)

Preparation 66

To a suspension of lithium aluminum hydride (1.8 g) in tetrahydrofuran (200 ml) was added 3-(1-trityl-2,3-dihydro-1H-imidazo[1,2-b]pyrazol-7-yl)propanamide (10 g) at room temperature. The mixture was stirred at room temperature for 2.5 hours. After cooling on an ice bath, sodium fluoride (7.95 g) and water (3.4 ml) were added to the reaction mixture. The insoluble materials were removed by filtration. To the filtrate was added ethyl formate, and the mixture was refluxed for 24 hours. After evaporation of the solvent in vacuo, the residue was triturated with diisopropyl ether and dried in vacuo to give 3-(1-trityl-2,3-dihydro-1H-imidazo[1,2-b]pyrazol-7-yl)propylformamide (6.62 g).

¹H-NMR(DMSO-d₆) δ1.0–1.2 (4H, m), 2.69 (2H, td, J=5.7 Hz), 3.42 (2H, t, J=7.4 Hz), 3.82 (2H, t, J=7.4 Hz), 6.97 (1H, s), 7.2–7.5 (15H, m), 7.80 (1H, t, J=5.7 Hz), 7.92 (1H, s)

ESI-MASS: m/z=459(M+Na)

Preparation 67

To a solution of benzhydryl 7β-tert-butoxycarbonylamino-3-chloromethyl-3-cephem-4-carboxylate (2.5 g) in a mixture of N,N-dimethylformamide (5 ml) and methylene chloride (8 ml) was added sodium iodide (728 mg), and the mixture was stirred at room temperature for 30 minutes. To the reaction mixture was added 3-(1-trityl-2,3-dihydro-1H-imidazo [1,2-b)pyrazol-7-yl)propylformamide (6.36 g). The whole mixture was stirred at room temperature for 26 hours and poured into a mixture of ethyl acetate and water. The aqueous layer was separated, and the organic layer was washed with brine, dried over anhydrous magnesium sulfate and filtered. The filtrate was concentrated to about 10 ml in vacuo. The concentrate was poured into diisopropyl ether (300 ml), and the resulting precipitate was collected by filtration and dried in vacuo. To a solution of the resulting solid in methylene chloride (21 ml) were added anisole (7 ml) and trifluoroacetic acid (14 ml). The resulting solution was stirred at room temperature for 3 hours and poured into diisopropyl ether. The resulting precipitate was collected by filtration and dried in vacuo to give 7β-amino-3-[2,3-dihydro-7-(3-formamidopropyl)-5-(1H-imidazo[1,2-b]pyrazolio)]methyl-3-cephem-4-carboxylate bistrifluoroacetate (4.17 g). This product was used in the next step without further purification.

EXAMPLE 23

To a solution of crude 7β-amino-3-[2,3-dihydro-7-(3-formamidopropyl)-5-(1H-imidazo[1,2-b]pyrazolio)]methyl-3-cephem-4-carboxylate bistrifluoroacetate (4.17 g) and N-trimethylsilylacetamide (8.63 g) in a mixed solvent of N,N-dimethylformamide (20 ml) and tetrahydrofuran (20 ml) was added (Z)-2-(5-amino-1,2,4-thiadiazol-3-yl)-2-(1-tert-butoxycarbonyl-1-methylethoxyimino)acetyl chloride hydrochloride salt (2.53 g) under ice-cooling. The mixture was stirred under ice-cooling for 2 hours. The reaction mixture was poured into ethyl acetate, and the mixture was stirred for 30 minutes. The resulting precipitate was collected by filtration, washed with successively ethyl acetate and diisopropyl ether, and dried in vacuo to give a solid (2.2 g).

To a suspension of the resulting solid in methylene chloride (9 ml) were added anisole (3 ml) and trifluoroacetic acid (6 ml) under ice-cooling. The resulting solution was stirred at room temperature for 3 hours and poured into diisopropyl ether. The resulting precipitate was collected by filtration and dried in vacuo. The obtained powder was dissolved in a phosphate buffer (pH 7) and adjusted to about pH 6 with saturated aqueous sodium hydrogencarbonate solution. The solution containing a objective compound was purified by preparative HPLC utilizing ODS column. The eluate containing a desired product was concentrated in vacuo. The concentrate was adjusted to about pH 2 with concentrated hydrochloric acid and chromatographed on Diaion® HP-20 (Mitsubishi Chemical Corporation) eluting with 20% aqueous 2-propanol. The eluate was evaporated in vacuo and lyophilized to give 7β-[(Z)-2-(5-amino-1,2,4-thiadiazol-3-yl)-2-(1-carboxy-1-methylethoxyimino)acetamido]-3-[2,3-dihydro-7-(3-formamidopropyl)-5-(1H-imidazo[1,2-b]pyrazolio)]methyl-3-cephem-4-carboxylate (391.2 mg).

¹H-NMR(D₂O) δ1.55 (6H, s), 1.76 (2H, quint., J=7.0 Hz), 2.40 (2H, t, J=7.0 Hz), 3.22 (2H, t, J=7.0 Hz), 3.23 (1H, d, J=17.7 Hz), 3.46 (1H, d, J=17.7 Hz), 4.0–4.4 (4H, m), 4.87 (1H, d, J=15.4 Hz), 5.05 (1H, d, J=15.4 Hz), 5.23 (1H, d, J=4.8 Hz), 5.84 (1H, d, J=4.8 Hz), 7.83 (1H, s), 8.02 (1H, s)

IR(KBr): 1776.1, 1668.1, 1656.6, 1608.3 cm⁻¹

ESI-MASS: m/z=661(M–H)

EXAMPLE 24

To a solution of 7β-[(Z)-2-(5-amino-1,2,4-thiadiazol-3-yl)-2-(1-carboxy-1-methylethoxyimino)acetamido]-3-[2,3-dihydro-7-(3-formamidopropyl)-5-(1H-imidazo[1,2-b]pyrazolio)]methyl-3-cephem-4-carboxylate (386 mg) in methanol (3.9 ml) was added concentrated hydrochloric acid (0.386 ml) at room temperature. The mixture was stirred at room temperature for 3 hours. The reaction mixture was poured into a mixture of ethyl acetate (300 ml) and acetone (100 ml). The resulting precipitate was collected by filtration and dried in vacuo. The obtained powder was dissolved in a phosphate buffer (pH 7) and adjusted to about pH 6 with saturated aqueous sodium hydrogencarbonate solution. The solution containing the objective compound was purified by preparative HPLC utilizing ODS column. The eluate containing a desired product was concentrated in vacuo. The concentrate was adjusted to about pH 2 with concentrated hydrochloric acid and chromatographed on Diaion® HP-20 (Mitsubishi Chemical Corporation) eluting with 20% aqueous 2-propanol. The eluate was evaporated in vacuo and lyophilized to give 7β-[(Z)-2-(5-amino-1,2,4-thiadiazol-3- yl)-2-(1-carboxy-1-methylethoxyimino)acetamido]-3-[2,3-dihydro-7-(3-aminopropyl)-5-(1H-imidazo[1,2-b]pyrazolio)]methyl-3-cephem-4-carboxylate (84 mg). $^1$H-NMR (D$_2$O) δ1.52 (3H, s), 1.53 (3H, s), 1.89 (2H, quint., J=7.5 Hz), 2.46 (2H, t, J=7.5 Hz), 3.00 (2H, t, J=7.5 Hz), 3.25 (1H, d, J=17.7 Hz), 3.50 (1H, d, J=17.7 Hz), 4.0–4.4 (4H, m), 4.87 (1H, d, J=15.4 Hz), 5.05 (1H, d, J=15.4 Hz), 5.25 (1H, d, J=4.8 Hz), 5.84 (1H, d, J=4.8 Hz), 7.88 (1H, s)

IR(KBr): 1772.3, 1648.8, 1585.2, 1537.0, 1400.1 cm$^{-1}$

ESI-MASS: m/z=635(M+H)

Preparation 68

2-(5-Amino-4-cyano-1H-pyrazol-1-yl)acetamide

The title compound was obtained from ethyl 2-(5-amino-4-cyano-1H-pyrazol-1-yl)acetate in the same manner as in Preparation 64.

$^1$H-NMR(DMSO-d$_6$) δ4.53 (2H, s), 6.56 (2H, s), 7.24 (1H, s), 7.42 (1H, s), 7.52 (1H, s)

APC-MASS: m/z=166(M+H)

Preparation 69

2-[4-Cyano-5-(tritylamino)-1H-pyrazol-1-yl]acetamide

The title compound was obtained from 2-(5-amino-4-cyano-1H-pyrazol-1-yl)acetamide in the same manner as in Preparation 27.

$^1$H-NMR(DMSO-d$_6$) δ4.80 (2H, s), 7.1–7.4 (15H, m), 7.42 (1H, s), 7.54 (1H, s), 7.75 (1H, s), 7.91 (1H, s)

APC-MASS: m/z=406

Preparation 70

To a suspension of lithium aluminum hydride (3.73 g) in tetrahydrofuran (100 ml) was added 2-[4-cyano-5-(tritylamino)-1H-pyrazol-1-yl]acetamide (5 g) at room temperature. The mixture was refluxed for 23 hours. After cooling on an ice bath, sodium fluoride (16.5 g) and water (7.1 ml) were added to the reaction mixture. The insoluble materials were removed by filtration. The filtrate was evaporated in vacuo and triturated with diisopropyl ether to give 1-(2-aminoethyl)-4-(aminomethyl)-5-tritylaminopyrazole (2.17 g).

$^1$H-NMR(DMSO-d$_6$) δ2.55 (2H, t, J=6.4 Hz), 2.84 (2H, s), 3.17 (2H, t, J=6.4 Hz), 6.04 (1H, s), 7.1–7.4 (16H, m)

IR(KBr): 3342.0, 1562.1, 1473.3, 756.0, 703.9 cm$^{-1}$

ESI-MASS: m/z=420(M+Na)

Preparation 71

To a solution of 1-(2-aminoethyl)-4-(aminomethyl)-5-tritylaminopyrazole (1 g) in tetrahydrofuran (35 ml) was added di-tert-butyl dicarbonate (1.65 g). The mixture was stirred at room temperature for 16 hours. The reaction mixture was added to a mixture of ethyl acetate and water. The aqueous layer was separated, and the organic layer was dried over anhydrous magnesium sulfate and filtered. The filtrate was concentrated in vacuo and triturated with hexane to give 1-(2-tert-butoxycarbonylaminoethyl)-4-(tert-butoxycarbonylaminomethyl)-5-tritylaminopyrazole (1.27 g).

$^1$H-NMR(DMSO-d$_6$) δ1.36 (9H, s), 1.39 (9H, s), 2.8–3.2 (4H, m), 3.27 (2H, d, J=5.7 Hz), 5.81 (1H, s), 6.35 (1H, t, J=5.7 Hz), 6.69 (1H, t, J=5.7 Hz), 6.98 (1H, s), 7.0–7.4 (15H, m)

IR(KBr): 3351.7, 3230.2, 2979.5, 1687.4, 1521.6, 1170.6, 703.9 cm$^{-1}$

APC-MASS: m/z=597

EXAMPLE 25

7β-[(Z)-2-(5-Amino-1,2,4-thiadiazol-3-yl)-2-(1-carboxy-1-methylethoxyimino)acetamido]-3-(3-amino-4-aminomethyl-2-(2-aminoethyl)-1-pyrazolio]methyl-3-cephem-4-carboxylate The title compound was obtained from benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate and 1-(2-tert-butoxycarbonylaminoethyl)-4-(tert-butoxycarbonylaminomethyl)-5-tritylaminopyrazole in the same manner as in Example 10.

$^1$H-NMR(D$_2$O) δ1.54 (6H, s), 3.06 (1H, d, J=17.9 Hz), 3.37 (2H, t, J=7.4 Hz), 3.57 (1H, d, J=17.9 Hz), 4.09 (2H, s), 4.5–4.9 (2H, m), 5.04 (1H, d, J=16.1 Hz), 5.27 (1H, d, J=16.1 Hz), 5.30 (1H, d, J=4.8 Hz), 5.82 (1H, d, J=4.8 Hz), 8.17 (1H, s)

IR(KBr): 3363.2, 3180.0, 1770.3, 1648.8, 1592.9, 1396.2 cm$^{-1}$

Preparation 72

Under a nitrogen atmosphere, 10% palladium on active carbon (125 g) and methanol (3.75 L) were placed in a 5.0 L of three-necked flask. To the mixture was added 5-amino-4-cyano-1-(2-hydroxyethyl)-1H-pyrazole (250 g). The mixture was stirred at room temperature for 1 hour under a hydrogen atmosphere. To the reaction mixture was added 4N hydrogen chloride solution in methanol (1.65 L), and the mixture was stirred at room temperature for 1.5 hours under a hydrogen atmosphere. To the reaction mixture was added water (1.2 L). The catalyst was filtered off and washed with 50% aqueous methanol, and the filtrate was evaporated in vacuo. The residue was triturated with isopropanol/ethyl acetate (1:1). The precipitate was collected by filtration on a glass filter, washed with ethyl acetate and dried in vacuo to give 5-amino-4-aminomethyl-1-(2-hydroxyethyl)-1H-pyrazole dihydrochloride (358 g) as a white solid.

$^1$H-NMR(DMSO-d$_6$) δ3.71 (2H, t, J=5.1 Hz), 3.86 (2H, d, J=5.4 Hz), 4.22 (2H, t, J=5.1 Hz), 7.99 (1H, s), 8.20–8.60 (2H, br)

IR(Br): 1647, 1595, 1489, 1061, 878 cm$^{-1}$

APC-MASS: m/z=157.3(M+H$^+$)

Preparation 73

5-Amino-4-aminomethyl-1-(2-hydroxyethyl)-1H-pyrazole dihydrochloride (105 g) was dissolved in a mixture of tetrahydrofuran (1700 ml) and water (170 ml), and the pH of the solution was adjusted to 9 with 3N aqueous sodium hydroxide solution. To the solution was added dropwise a solution of di-tert-butyl dicarbonate (173 g) in tetrahydrofuran (860 ml), while 3N aqueous sodium hydroxide solution was added to keep the pH of the reaction mixture 8.5–9.0. The stirring was continued for another 1 hour. The reaction mixture was extracted with ethyl acetate. The organic layer was washed with brine, dried over magnesium sulfate, filtered, and evaporated in vacuo. The residue was triturated with diisopropyl ether. The precipitate was collected by filtration on a glass filter, washed with diisopropyl ether and dried in vacuo to give 5-amino-4-(tert-butoxycarbonylaminomethyl)-1-(2-hydroxyethyl)-1H-pyrazole (118 g). $^1$H-NMR(DMSO-d$_6$) δ1.37 (9H, s), 3.58–3.66 (2H, m), 3.78 (2H, d, J=6.0 Hz), 3.88 (2H, t, J=6.1 Hz), 4.88 (1H, t, J=5.1 Hz), 4.97 (2H, br s), 6.96 (1H, s), 6.95–7.10 (1H, m)

IR(KBr): 1672, 1631, 1527, 1434, 1277, 1165, 866, 789 cm$^{-1}$

APC-MASS: m/z=257.13 (M+H$^+$)

Preparation 74

To a solution of 5-amino-4-(tert-butoxycarbonylaminomethyl)-1-(2-hydroxyethyl)-1H-pyrazole (243 g) in N,N-dimethylformamide (1.82 L) was added triphenylmethyl chloride (581 g), triethylamine (452 ml) and N,N-dimethylaminopyridine (9.91 g) successively. The reaction mixture was stirred at 70° C. overnight. After cooling to room temperature, the reaction mixture was diluted with ethyl acetate, washed with water (twice) and brine, dried over magnesium sulfate and filtered. The filtrate was evaporated in vacuo. The residue was purified by silica gel column chromatography to give 4-(tert-butoxycarbonylaminomethyl)-5-(tritylamino)-1-[2-(trityloxy)ethyl]-1H-pyrazole, which was crystallized from diisopropyl ether/hexane (1:2). The resulting crystals were collected by filtration on a glass filter, washed with diisopropyl ether/hexane (1:2) and dried in vacuo to give the objective compound (480 g).

$^1$H-NMR(DMSO-$d_6$) δ1.30 (9H, s), 2.91 (2H, t, J=5.5 Hz), 3.29 (4H, m), 5.88 (1H, s), 6.53 (1H, t-like), 7.06 (1H, s), 7.10–7.40 (15H, m)

IR(KBr): 1693, 1495, 1446, 1165, 758, 702 cm$^{-1}$

APC-MASS: m/z=763.3(M+Na$^+$)

EXAMPLE 26

To a solution of benzhydryl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (5.82 g) in N,N-dimethylformamide (12 ml) was added sodium iodide (1.44 g). After stirring at room temperature for 1 hour, 4-(tert-butoxycarbonylaminomethyl)-5-(tritylamino)-1-[2-(trityloxy)ethyl]-1H-pyrazole (14.8 g) was added to the mixture. The stirring was continued at 35° C. for 24 hours. The resulting mixture was poured into water and extracted with ethyl acetate. The organic layer was washed with brine, dried over magnesium sulfate, filtered and evaporated in vacuo. The residue was dissolved in ethyl acetate (50 ml) and added to diisopropyl ether (500 ml) dropwise. The resulting precipitate was collected by filtration. The filter cake was washed with diisopropyl ether and dried over phosphorous pentoxide in vacuo. The solid (15.6 g) was dissolved in dichloromethane (47 ml), and to the solution were added anisole (16 ml) and trifluoroacetic acid (32 ml) successively. After stirring at room temperature for 3 hours, the reaction mixture was poured into diisopropyl ether (500 ml). The precipitate was collected by filtration, washed with diisopropyl ether and dried over phosphorous pentoxide in vacuo. The crude product was dissolved in a phosphate buffer (pH 7.0) and purified by preparative HPLC (eluent: pH 7.0 phosphate buffer and acetonitrile). The eluate was subjected to column chromatography on Diaion® HP-20 (Mitsubishi Chemical Corporation) and freeze-dried to give 7β-[(Z)-2-(5-amino-1,2,4-thiadiazol-3-yl)-2-(1-carboxy-1-methylethoxyimino)acetamido]-3-[3-amino-4-aminomethyl-2-(2-hydroxyethyl)-1-pyrazolio]methyl-3-cephem-4-carboxylate (940 mg).

EXAMPLE 27

7β-[(Z)-2-(5-Amino-1,2,4-thiadiazol-3-yl)-2-(1-carboxy-1-methylethoxyimino)acetamido]-3-[3-amino-4-aminomethyl-2-(2-hydroxyethyl)-1-pyrazolio]methyl-3-cephem-4-carboxylate (5.0 g) was dissolved in water (100 ml), and 2.0 M sulfuric acid (4.0 ml) was added to the solution. The mixture was freeze-dried to give crude 7β-[(Z)-2-(5-amino-1,2,4-thiadiazol-3-yl)-2-(1-carboxy-1-methylethoxyimino)acetamido]-3-[3-amino-4-aminomethyl-2-(2-hydroxyethyl)-1-pyrazolio]methyl-3-cephem-4-carboxylate hydrogensulfate (5.18 g) as an amorphous solid. The amorphous solid (1.0 g) was dissolved in water (1.0 ml). To the solution was added acetonitrile (5.0 ml) dropwise. After stirring at room temperature for 2 hours, white crystals precipitated. The precipitated crystals were collected by filtration on a glass filter, washed with a small amount of water/acetonitrile (1:5) and dried under reduced pressure to give 7β-[(Z)-2-(5-amino-1,2,4-thiadiazol-3-yl)-2-(1-carboxy-1-methylethoxyimino)acetamido]-3-[3-amino-4-aminomethyl-2-(2-hydroxyethyl)-1-pyrazolio]methyl-3-cephem-4-carboxylate hydrogensulfate (880 mg) as white crystals. $^1$H-NMR(D$_2$O) δ1.61(6H, s), 3.20 and 3.53 (2H, ABq, J=18.0 Hz), 3.87 (2H, t, J=4.6 Hz), 4.09 (2H, s), 4.38 (2H, t, J=4.6 Hz), 5.16 (2H, s), 5.28 (1H, d, J=4.8 Hz), 5.88 (1H, d, J=4.8 Hz), 8.10 (1H, s)

IR(KBr): 1782, 1708, 1649, 1161, 1113 cm$^{-1}$

ESI-MASS: m/z=625.2 (M+H$^+$)

Preparation 75

To a mixture of lithium aluminum hydride (32.6 g) in tetrahydrofuran (1.3 L) was added (2E)-3-[1-methyl-5-(tritylamino)-1H-pyrazol-4-yl]-2-propenonitrile (101.6 g) under ice-cooling. The mixture was refluxed for 4 hours. After cooling on an ice bath, sodium fluoride (100 g) and water (100 ml) were added to the reaction mixture. The insoluble materials were removed by filtration. The filtrate was concentrated in vacuo to give 4-(3-aminopropyl)-1-methyl-5-tritylamino-1H-pyrazole (88.9 g). $^1$H-NMR (DMSO-$d_6$) δ1.00–1.22 (2H, m), 1.70–1.90 (2H, m), 2.15–2.35 (2H, m), 2,74 (3H, s), 5.70 (1H, s), 6.97 (1H, s), 7.10–7.38 (15H, m)

ESI-MASS: m/z=397.4(M+H$^+$)

Preparation 76

To a solution of 4-(3-aminopropyl)-1-methyl-5-tritylamino-1H-pyrazole (75 g) in tetrahydrofuran (700 ml) was added di-tert-butyl dicarbonate (49.5 g). The reaction mixture was stirred at room temperature for 3 hours. After evaporation of the solvent in vacuo, the residue was triturated with diisopropyl ether and dried in vacuo to give tert-butyl 3-[1-methyl-5-(tritylamino)-1H-pyrazol-4-yl]propylcarbamate (71.7 g).

$^1$H-NMR(DMSO-$d_6$) δ1.10–1.25 (2H, m), 1.39 (9H, s), 1.65–1.85 (2H, m), 2.60–2.80 (2H, m), 2.75 (3H, s), 5.66 (1H, s), 6.50–6.70 (1H, m), 6.99 (1H, s), 7.05–7.35 (15H, m)

EXAMPLE 28

To a suspension of a mixture of benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate (40 g) and sodium iodide (8 g) in N,N-dimethylformamide (120 ml) and methylene chloride (80 ml) was added tert-butyl 3-[1-methyl-5-(tritylamino)-1H-pyrazol-4-yl]propylcarbamate (60 g), and the mixture was stirred at room temperature for 16 hours. The reaction mixture was added to a mixture of ethyl acetate and water. The organic layer was separated and dried over magnesium sulfate. The magnesium sulfate was filtered off, and the filtrate was evaporated to about 20 ml under reduced pressure. The concentrate was poured into diisopropyl ether (150 ml), and the resulting precipitate was collected by filtration and dried in vacuo. The precipitate was purified by column chromatography on Diaion® PA306 (Mitsubishi Chemical Corporation) TFA form (400 ml) eluting with tetrahydrofuran. The eluate was concentrated in vacuo. The residue was dissolved in methylene chloride (200 ml), and to the solution were added anisole (70 ml) and trifluoroacetic acid (140 ml). The mixture was stirred at room temperature for 3 hours and poured into diisopropyl ether. The resulting precipitate was collected by filtration and dried in vacuo. The obtained powder was dissolved in a phosphate buffer (pH 7) and adjusted to about pH 6 with saturated aqueous sodium hydrogencarbonate solution. The solution containing the objective compound was purified by preparative HPLC utilizing ODS column. The eluate containing a desired product was concentrated in vacuo. The concentrate was adjusted to about pH 1 with concentrated hydrochloric acid and chromatographed on Diaion® HP-20 (Mitsubishi Chemical Corporation) eluting with 20% aqueous 2-propanol. The eluate was evaporated in vacuo and lyophilized to give 7β-[(Z)-2-(5-amino-1,2,4-thiadiazol-3-yl)-2-(1-carboxy-1-methylethoxyimino)acetamido]-3-[3-amino-4-(3-aminopropyl)-2-methyl-1-pyrazolio]methyl-3-cephem-4-carboxylate (6.1 g).

$^1$H-NMR(D$_2$O) δ1.52 (6H, s), 1.78–2.00 (2H, m), 2.48 (2H, t, J=7.5 Hz), 3.04 (2H, t, J=8.1 Hz), 3.15 and 3.38 (2H, ABq, J=17.6 Hz), 3.68 (3H, s), 4.90 and 5.22 (2H, ABq, J=15.3 Hz), 5.24 (1H, d, J=4.8 Hz), 5.84 (1H, d, J=4.8 Hz), 7.78 (1H, s)

EXAMPLE 29

To a suspension of a mixture of benzhydryl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (330 g) and sodium iodide (74.8 g) in N,N-dimethylformamide (660 ml) was added tert-butyl 3-[1-methyl-5-(tritylamino)-1H-pyrazol-4-yl]propylcarbamate (282 g), and the mixture was stirred at room temperature for 16 hours. The reaction mixture was added to a mixture of ethyl acetate and water. The organic layer was washed with water, brine and 10% aqueous sodium trifluoroacetate solution, and then dried over magnesium sulfate. The magnesium sulfate was filtered off, and the filtrate was evaporated to about 3.3 kg under reduced pressure. The concentrate was poured into diisopropyl ether (33 L), and the resulting precipitate was collected by filtration and dried in vacuo.

To a solution of the resulting solid in methylene chloride (1600 ml) were added anisole (530 ml) and trifluoroacetic acid (1600 ml). The mixture was stirred at room temperature for 3 hours and poured into diisopropyl ether. The resulting precipitate was collected by filtration and dried in vacuo. The obtained powder was dissolved in a phosphate buffer (pH 7) and adjusted to about pH 6 with saturated aqueous sodium hydrogencarbonate solution. The solution containing the objective compound was purified by preparative HPLC utilizing ODS column. The eluate containing a desired product was concentrated in vacuo. The concentrate was adjusted to about pH 2 with concentrated hydrochloric acid and chromatographed on Diaion® HP-20 (Mitsubishi Chemical Corporation) eluting with 20% aqueous 2-propanol. The eluate was evaporated in vacuo and lyophilized to give 7β-[(Z)-2-(5-amino-1,2,4-thiadiazol-3-yl)-2-(1-carboxy-1-methylethoxyimino)acetamido]-3-[3-amino-4-(3-aminopropyl)-2-methyl-1-pyrazolio]methyl-3-cephem-4-carboxylate (78.4 g).

EXAMPLE 30

A solution of 7β-[(Z)-2-(5-amino-1,2,4-thiadiazol-3-yl)-2-(1-carboxy-1-methylethoxyimino)acetamido]-3-[3-amino-4-(3-aminopropyl)-2-methyl-1-pyrazolio]methyl-3-cephem-4-carboxylate (22.5 g) in water (180 ml) was purified by preparative HPLC utilizing ODS column. The eluate containing a desired product was concentrated to about 1.5 L in vacuo. The concentrate was adjusted to about pH 1 with concentrated hydrochloric acid and chromatographed on Diaion® HP-20 (Mitsubishi Chemical Corporation) (1.5 L) eluting with 20% aqueous 2-propanol. The eluate was concentrated to about 400 ml in vacuo. To the solution was added 2 mol/l sulfuric acid (16 ml), and then the mixture was lyophilized to give amorphous powder of sulfuric acid salt (16 g). The powder was dissolved in water (70 ml) and 2-propanol (80 ml) under stirring at room temperature. The stirring was continued at room temperature for 4 hours. The precipitated crystals were collected by filtration to give 7β-[(Z)-2-(5-amino-1,2,4-thiadiazol-3-yl)-2-(1-carboxy-1-methylethoxyimino)acetamido]-3-[3-amino-4-(3-aminopropyl)-2-methyl-1-pyrazolio]methyl-3-cephem-4-carboxylate hydrogensulfate (13 g).

$^1$H-NMR (D$_2$O) δ1.61 (6H, s), 1.95 (2H, quintet, J=7.5 Hz), 2.48 (2H, t, J=7.5 Hz), 3.05 (2H, t, J=7.5 Hz), 3.18 and 3.39 (2H, ABq, J=17.9 Hz), 3.67 (3H, s), 4.90 and 5.22 (2H, ABq, J=15.3 Hz), 5.24 (1H, d, J=4.8 Hz), 5.86 (1H, d, J=4.8 Hz), 7.78 (1H, s)

IR(KBr): 1781, 1728, 1680, 1635, 1599, 1406, 1315, 1132, 1101, 995 cm$^{-1}$

ESI-MASS: m/z=623.2 (M+H$^+$)

X-ray powder diffraction analysis (by Philips MPD 1880 X-ray Powder Diffraction System)

| 2θ | intensity |
|------|-----------|
| 8.5 | 180 |
| 14 | 160 |
| 14.5 | 500 |
| 15.3 | 400 |
| 15.5 | 300 |
| 16.5 | 420 |
| 17.3 | 600 |
| 19 | 410 |
| 19.4 | 260 |
| 20 | 240 |
| 24.5 | 240 |
| 25 | 430 |
| 26 | 400 |
| 28 | 250 |

X-ray: Monochromated CnKα radiation

Voltage: 40 KV/Current: 30 mA

This application is based on application No. PR 4690 filed in Australia on May 1, 2001, and application No. PR 5834 filed in Australia on Jun. 20, 2001, the content of which is incorporated hereinto by reference.

The invention claimed is:
1. A compound of the formula:

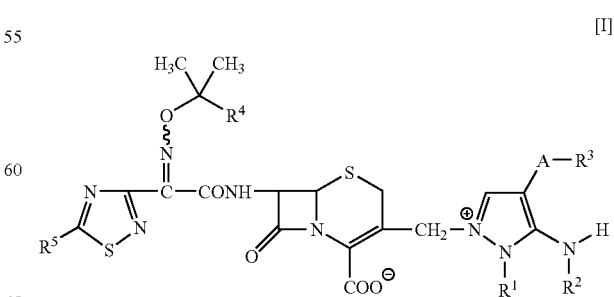

wherein

A is lower alkylene or lower alkenylene;

$R^1$ is lower alkyl, hydroxy(lower)alkyl, protected hydroxy (lower)alkyl in which the hydroxy group is protected with an acyl group or an aryl(lower)alkyl group, amino (lower)alkyl or an amino(lower)alkyl in which the amino group is protected by an acyl group or a substituted or unsubstituted aryl(lower)alkyl group, and $R^2$ is hydrogen or an amino protecting group selected from the group consisting of an acyl group or a substituted or unsubstituted aryl(lower)alkyl group, or $R^1$ and $R^2$ are bonded together and form lower alkylene;

$R^3$ and $R^5$ are, independently, amino or amino protected with an acyl group or a substituted or unsubstituted aryl(lower)alkyl group; and $R^4$ is carboxy or esterified carboxy, or a pharmaceutically acceptable salt thereof.

2. The compound of claim 1 wherein $R^1$ is lower alkyl, hydroxy(lower)alkyl, aryl(lower)alkyloxy(lower)alkyl, amino(lower)alkyl or acylamino (lower)alkyl, and $R^2$ is hydrogen, aryl(lower)alkyl or acyl, or $R^1$ and $R^2$ are bonded together and form lower alkylene;

$R^3$ and $R^5$ are, independently, amino or acylamino; and $R^4$ is carboxy or esterified carboxy, or a pharmaceutically acceptable salt thereof.

3. The compound of claim 2 wherein $R^1$ is lower alkyl, hydroxy(lower)alkyl, aryl(lower)alkyloxy(lower)alkyl, amino(lower)alkyl, (lower)alkanoylamino(lower)alkyl, or (lower)alkoxycarbonylamino (lower)alkyl, and $R^2$ is hydrogen, aryl(lower)alkyl, lower alkanoyl or lower alkoxycarbonyl, or $R^1$ and $R^2$ are bonded together and form lower alkylene;

$R^3$ and $R^5$ are, independently, amino, lower alkanoylamino or lower alkoxycarbonylamino; and $R^4$ is carboxy or lower alkoxycarbonyl, or a pharmaceutically acceptable salt thereof.

4. The compound of claim 3 wherein $R^1$ is lower alkyl, hydroxy(lower)alkyl or amino(lower) alkyl, and $R^2$ is hydrogen, or $R^1$ and $R^2$ are bonded together and form lower alkylene;

$R^3$ and $R^5$ are amino; and $R^4$ is carboxy, or a pharmaceutically acceptable salt thereof.

5. A process for preparing a compound of the formula [I]:

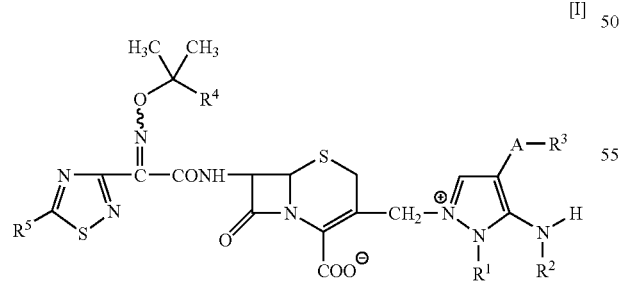

wherein

A is lower alkylene or lower alkenylene;

$R^1$ is lower alkyl, hydroxy(lower)alkyl, protected hydroxy (lower)alkyl in which the hydroxyl group is protected with an acyl group or an aryl(lower)alkyl group, amino (lower)alkyl or an amino(lower)alkyl in which the amino group is protected by an acyl group or a substituted or unsubstituted aryl(lower)alkyl group, and $R^2$ is hydrogen or an amino protecting group selected from the group consisting of an acyl group or a substituted or unsubstituted aryl(lower)alkyl group, or $R^1$ and $R^2$ are bonded together and form lower alkylene;

$R^3$ and $R^5$ are, independently, amino or amino protected with an acyl group or a substituted or unsubstituted aryl(lower)alkyl group; and $R^4$ is carboxy or esterified carboxy, or a salt thereof, which comprises (1) reacting a compound of the formula [II]:

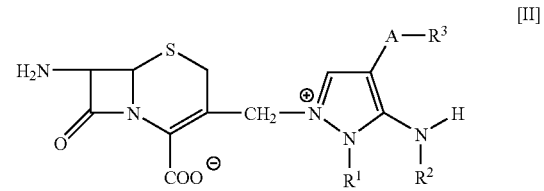

wherein A, $R^1$, $R^2$ and $R^3$ are each as defined above, or its reactive derivative at the amino group, or a salt thereof with a compound of the formula [III]:

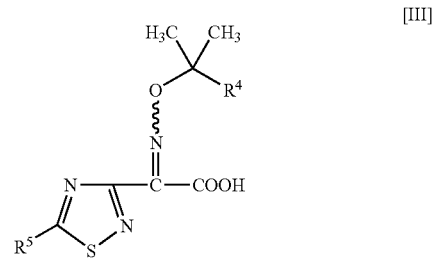

wherein $R^4$ and $R^5$ are each as defined above, or its reactive derivative at the carboxy group, or a salt thereof to give a compound of the formula [I]:

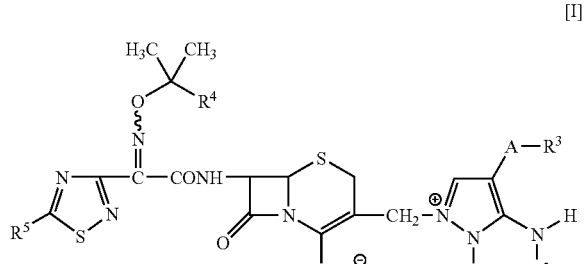

wherein A, $R^1$, $R^2$, $R^3$, $R^4$ and $R^5$ are each as defined above, or a salt thereof, or (2) subjecting a compound of the formula [Ia]:

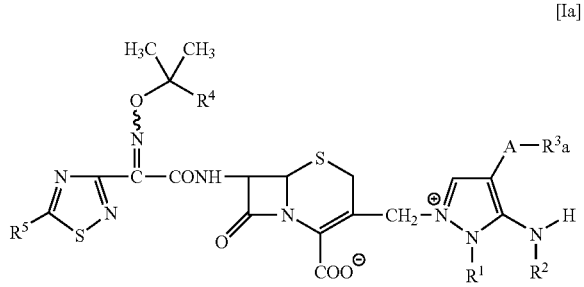

[Ia]

wherein A, $R^1$, $R^2$, $R^4$ and $R^5$ are each as defined above, and $R^3a$ an amino group protected by an acyl group or a substituted or unsubstituted aryl(lower)alkyl group, or a salt thereof to elimination reaction of the amino protecting group to give a compound of the formula [Ib]:

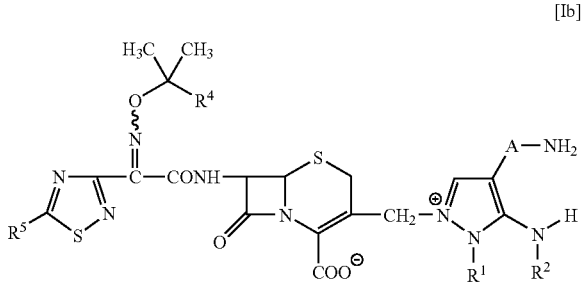

[Ib]

wherein A, $R^1$, $R^2$, $R^4$ and $R^5$ are each as defined above, or a salt thereof, or (3) reacting a compound of the formula [VI]:

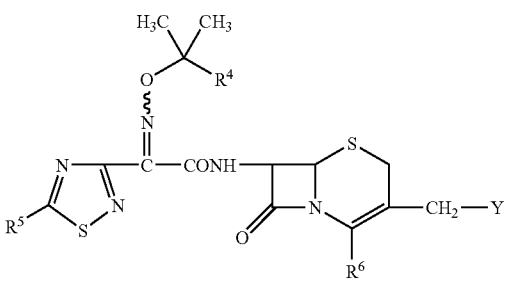

[VI]

wherein $R^4$ $R^5$ are each as defined above, $R^6$ is an esterfied carboxy group, and Y is a leaving group, or a salt thereof with a compound of the formula [VII]:

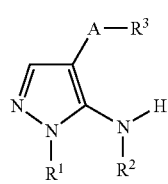

[VII]

wherein A, $R^1$, $R^2$, and $R^3$ are each as defined above, or a salt thereof to give a compound of the formula [VIII]:

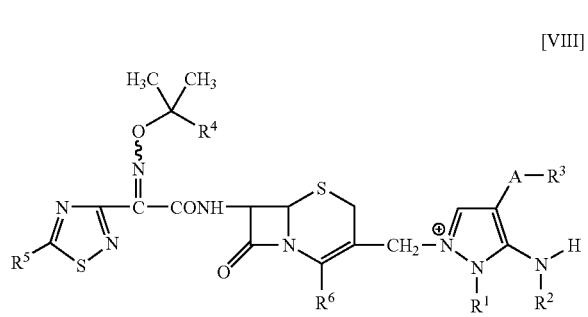

[VIII]

wherein A, $R^1$, $R^2$, $R^3$, $R^4$, $R^5$, and $R^6$ are each as defined above, or a salt thereof, and subjecting the compound of the formula [VIII] or a salt thereof to elimination reaction of the carboxy protecting group, to give a compound of the formula [I]:

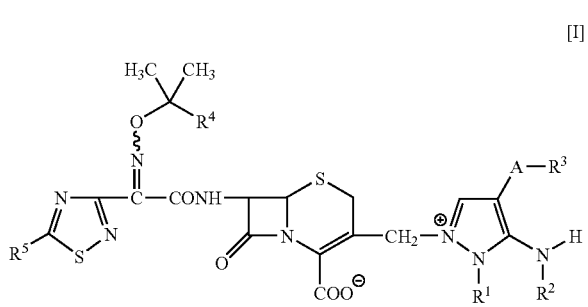

[I]

wherein A, $R^1$, $R^2$, $R^3$, $R^4$, and $R^5$ are each as defined above, or a salt thereof.

6. A pharmaceutical composition, comprising a compound of claim 1 or a pharmaceutically acceptable salt thereof in admixture with a pharmaceutically acceptable carrier.

7. A method of making the pharmaceutical composition of claim 6, comprising combining the compound or a pharmaceutically acceptable salt thereof with the pharmaceutically acceptable carrier.

8. A method of treating an infectious disease caused by a bacterium, comprising administering an effective amount of the compound of claim 1 or a pharmaceutically acceptable salt thereof to a human being or a non-human animal.

9. The method of claim 8, wherein the compound or the pharmaceutically acceptable salt thereof is administered to a human being.

10. A method of treating an infectious disease caused by a bacterium, comprising administering an effective amount of the pharmaceutical composition of claim 6 to a human being or a non-human animal.

11. The method of claim 10, wherein the pharmaceutical composition is administered to a human being.

* * * * *

UNITED STATES PATENT AND TRADEMARK OFFICE
CERTIFICATE OF CORRECTION

| | | |
|---|---|---|
| PATENT NO. | : 7,179,801 B2 | Page 1 of 1 |
| APPLICATION NO. | : 10/475845 | |
| DATED | : February 20, 2007 | |
| INVENTOR(S) | : Ohki et al. | |

It is certified that error appears in the above-identified patent and that said Letters Patent is hereby corrected as shown below:

On the title page, Item (30), the Foreign Application Priority Data information is incorrect. Item (30) should read:

-- (30)    Foreign Application Priority Data

May 1, 2001  (AU) ..................... PR 4690
Jun. 20, 2001 (AU) ..................... PR 5834 --

Signed and Sealed this

Seventeenth Day of April, 2007

JON W. DUDAS
*Director of the United States Patent and Trademark Office*